United States Patent [19]

Schulte-Elte et al.

[11] 4,264,467
[45] Apr. 28, 1981

[54] CYCLIC C₆ COMPOUNDS AND THEIR USE IN PERFUMES

[75] Inventors: Karl-Heinrich Schulte-Elte, Onex; Bruno Willhalm, Chene-Bourg; Fritz Gautschl, Commugny, all of Switzerland

[73] Assignee: Firmenich SA, Geneva, Switzerland

[21] Appl. No.: 935,263

[22] Filed: Aug. 21, 1978

Related U.S. Application Data

[60] Division of Ser. No. 708,075, Jul. 23, 1976, Pat. No. 4,147,672, which is a continuation-in-part of Ser. No. 541,988, Jul. 17, 1975, abandoned.

[30] Foreign Application Priority Data

Jan. 29, 1974 [CH] Switzerland .................... 1147/74

[51] Int. Cl.³ ................ C11D 9/44; C07C 69/74; A61K 7/46
[52] U.S. Cl. .................. 252/174.11; 252/107; 252/108; 252/132; 252/522 R; 260/340.9 R; 560/128; 560/231
[58] Field of Search .......... 252/107, 108, 132, 174.11, 252/522; 560/128, 231; 260/340.9 R

[56] References Cited

U.S. PATENT DOCUMENTS

| 3,238,260 | 3/1966 | Pasedach et al. | 252/522 R |
|---|---|---|---|
| 3,480,677 | 11/1969 | Menly et al. | 260/586 X |
| 3,487,102 | 12/1969 | Blumenthal | 252/522 |
| 3,887,625 | 6/1975 | Schulte-Elte | 260/617 R |
| 3,975,310 | 8/1976 | Kovats et al. | 252/522 |
| 4,144,199 | 3/1979 | Wille et al. | 252/522 |
| 4,147,672 | 4/1979 | Schulte-Elte | 252/522 |
| 4,147,737 | 4/1979 | Sprecker et al. | 260/586 R |

FOREIGN PATENT DOCUMENTS

| 2440607 | 3/1975 | Fed. Rep. of Germany | 560/128 |
|---|---|---|---|
| 1254198 | 11/1971 | United Kingdom | 560/231 |

*Primary Examiner*—P. E. Willis, Jr.
*Attorney, Agent, or Firm*—Pennie & Edmonds

[57] ABSTRACT

New oxygenated alicyclic derivatives useful as perfuming and odor modifying agents in the manufacture of perfumes or perfumed products, and as flavoring and taste-modifying agents in the aromatization of foodstuffs in general and imitation flavors for foodstuffs, beverages, animal feeds, pharmaceutical preparations and tobacco products.

Novel processes for the preparation of said alicyclic derivatives and compositions of matter relating to mixtures containing same.

10 Claims, No Drawings

CYCLIC C₆ COMPOUNDS AND THEIR USE IN PERFUMES

CROSS-REFERENCE TO RELATED APPLICATION

This is a division of application Ser. No. 708,075, filed July 23, 1976 and now U.S. Pat. No. 4,147,672, granted on Apr. 3, 1979, which in turn is a continuation-in-part of Ser. No. 541,988, filed July 17, 1975 and now abandoned.

BRIEF SUMMARY OF THE INVENTION

The compounds of the invention have the formula:

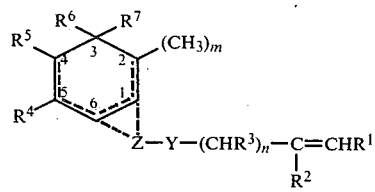

having a saturated ring or an isolated double bond in position 1, 4 or 6 or two double bonds in position 1 and 4, 1 and 5, or 4 and 6 of the ring as indicated by the dotted lines, and wherein:

m stands for integers 0 or 1;
n stands for integers 0, 1 or 2;
Z is bound to the ring carbon atoms in position 1 or 6 and represents the group —CO, —COR$^8$ or

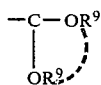

(wherein symbol R$^8$ represents an acyl group, and R$^9$ represents, when taken individually, an alkyl group having from 1 to 6 carbon atoms, or, when taken together, an alkylenyl group having from 2 to 6 carbon atoms);
Y represents an oxygen atom or a methylene group; each of the symbols R$^1$, R$^2$, R$^3$, R$^4$ and R$^5$ designates a hydrogen atom or one of them represents a methyl radical and each of the others a hydrogen atom, and each of symbols R$^6$ and R$^7$ represents an alkyl radical having from 1 to 3 carbon atoms or one of them represents an alkyl radical as defined above and the other a hydrogen atom.

The said compounds possess interesting organoleptic properties and accordingly represent useful perfuming and odour-modifying agents as well as flavouring and taste-modifying ingredients.

The present invention relates also to novel perfume compositions, as well as to certain perfumed articles.

This invention provides further a process for the preparation of the compounds of formula (I).

THE INVENTION

We have discovered that in view of their particular useful properties, the novel compounds of the invention can be used for modifying, enhancing or improving the organoleptic properties of foodstuffs, animal feeds, beverages, pharmaceutical preparations and tobacco products and for the manufacture of artificial flavouring compositions. The term "foodstuff" is used broadly, and includes coffee, tea and chocolate.

Typically, the compounds of formula (I) develop various flavour notes such as fruity, green, woody and oily notes. These flavouring characters are reminiscent of those developed by galbanum or Juniper oil.

Further, the compounds of formula (I) possess useful olfactive properties and, accordingly, can be used in the art of perfumery. They impart a variety of fragrance notes such as green, herbal, and fruity notes. These aromatic properties are reminiscent of the odour developed in particular by galbanum oil, and enable harmonious matches with a great variety of compositions such as floral, woody, green, chypre or animal type compositions. The incorporation of compounds (I) into perfume compositions brings about a distinct and lifting green character of great richness and power.

Compounds (I) are also particularly useful for the reconstruction of certain essential oils as well as for the manufacture of perfumed articles such as toilet soaps, cosmetics, detergents, household materials, waxes or air-refresheners.

The compounds of formula (I) can be used individually or in admixture of one with the others and/or in the presence of a diluent, a carrier or an excipient.

Typically, interesting odoriferous effects can be obtained when the compounds of formula (I) constitute from about 0.01 to 5% by weight of the total composition. Preferential proportion values are from about 0.01 to 2%. The compounds of the invention are particularly powerful and concentrations lying at the lower limit of the above given values are sufficient to promote interesting odoriferous effects.

It has to be understood however that the given ranges may be varied in order to achieve specific organoleptic effects. The examples which appear hereinafter illustrate certain applications within the scope of the invention, but they are not to be construed as limitations thereof.

The following are specific examples of compounds of formula (I):
1-(3,3-dimethyl-cyclohexyl)-pent-4-en-1-one,
1-(3,3-dimethyl-cyclohex-6-en-1-yl)-pent-4-en-1-one,
1-(3,3-dimethyl-cyclohex-1-en-1-yl)-pent-4-en-1-one,
1-(3,3-dimethyl-cyclohexa-4,6-dien-1-yl)-pent-4-en-1-one,
1-(3,3-dimethyl-cyclohexa-1,5-dien-1-yl)-pent-4-en-1-one,
1-(3,3-dimethyl-cyclohex-4-en-1-yl)-pent-4-en-1-one,
1-(3,3-dimethyl-cyclohex-1-en-1-yl)-pent-4-en-1-yl acetate,
1-(3,3-dimethyl-cyclohex-1-en-1-yl)-pent-4-en-1-yl formate,
1-(3,3-dimethyl-cyclohex-1-en-1-yl)-1,1-ethylenedioxy-pent-4-ene,
1-(3,3-dimethyl-cyclohex-6-en-1-yl)-pent-4-en-1-yl acetate,
1-(3,3-dimethyl-cyclohex-6-en-1-yl)-pent-4-en-1-yl formate,
1-(3,3-dimethyl-cyclohex-6-en-1-yl)-1,1-ethylenedioxy-pent-4-ene,
1-(3,3-dimethyl-cyclohexa-1,4-dien-1-yl)-pent-4-en-1-one,
1-(3,3-dimethyl-cyclohex-6-en-1-yl)-hex-5-en-1-one,
1-(3,3-dimethyl-cyclohex-1-ene-1-yl)-hex-4-en-1-one,
1-(3,3-dimethyl-cyclohex-6-en-1-yl)-hex-4-en-1-one,
1-(3,3-dimethyl-cyclohex-6-en-1-yl)-3-methyl-pent-4-en-1-one, 1-(3,3-dimethyl-cyclohex-1-en-1-yl)-3-methyl-pent-4-en-1-one,
1-(4,4-dimethyl-cyclohex-1-en-1-yl)-pent-4-en-1-one,
1-(3,3,4-trimethyl-cyclohex-6-en-1-yl)-pent-4-en-1-one,
1-(3,3,5-trimethyl-cyclohex-6-en-1-yl)-pent-4-en-1-one,
1-(3,3,5-trimethyl-cyclohex-1-en-1-yl)-pent-4-en-1-one,
1-(3,3,5-trimethyl-cyclohexa-4,6-dien-1-yl)-pent-4-en-1-one,
1-(3,3-dimethyl-cyclohex-6-en-1-yl)-but-3-en-1-one,
1-(3,3-dimethyl-cyclohex-6-en-1-yl)-3-methyl-but-3-en-1-one,
1-(3,3-dimethyl-cyclohex-6-en-1-yl)-2-methyl-but-3-en-1-one,
prop-2-en-1-yl-(3,3-dimethyl-cyclohex-6-en-1-yl)-carboxylate,
1-(3,5-dimethyl-cyclohex-6-en-1-yl)-pent-4-en-1-one,
1-(cis-3,4-dimethyl-cyclohex-6-en-1-yl)-pent-4-en-1-one,
1-(trans-3,4-dimethyl-cyclohex-6-en-1-yl)-pent-4-en-1-one,
1-(trans-3,4-dimethyl-cyclohex-1-en-1-yl)-pent-4-en-1-one,
1-(2,3,3-Trimethyl-cyclohex-6-en-1-yl)-pent-4-en-1-one,
1-(2,3,3-Trimethyl-cyclohexa-4,6-dien-1-yl)-pent-4-en-1-one,
1-(3,3-Dimethyl-cyclohexa-4,6-dien-1-yl)-3-methyl-pent-4-en-1-one,
1-(3,3-Dimethyl-cyclohexa-1,5-dien-1-yl)-3-methyl-pent-4-en-1-one,
1-(3,3-Dimethyl-cyclohexa-4,6-dien-1-yl)-hex-4-en-1-one and
1-(3,3-Dimethyl-cyclohexa-1,5-dien-1-yl)-hex-4-en-1-one.

The compounds of the invention are prepared in accordance with one of the processes described hereinafter and illustrated by the following reaction pathways:

PATHWAY I

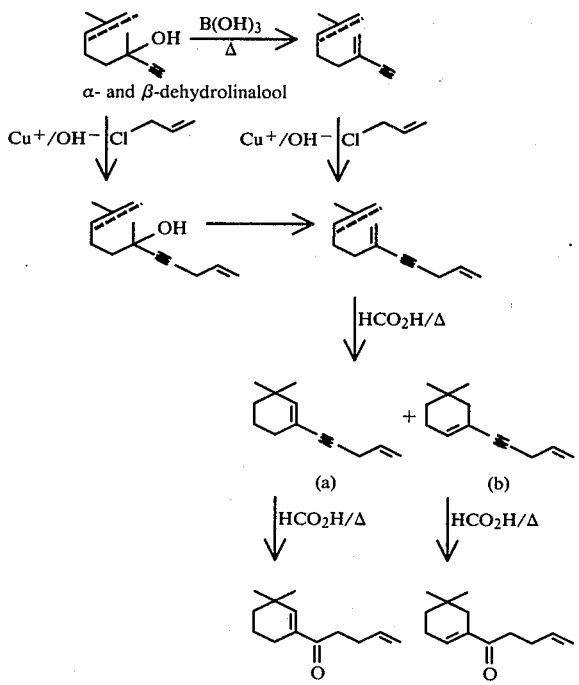

PATHWAY II

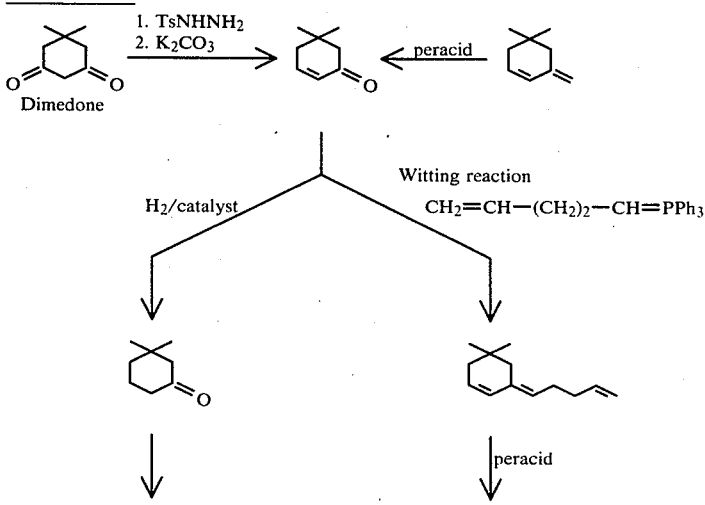

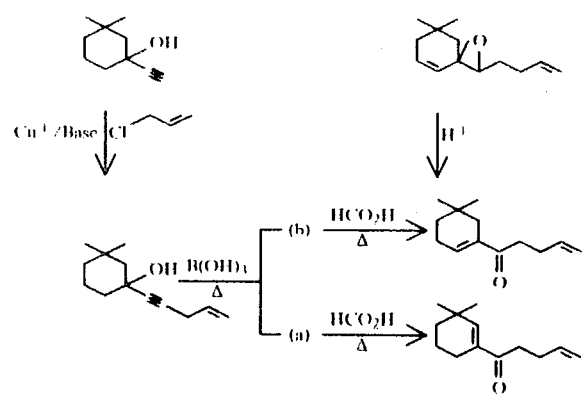
PATHWAY III
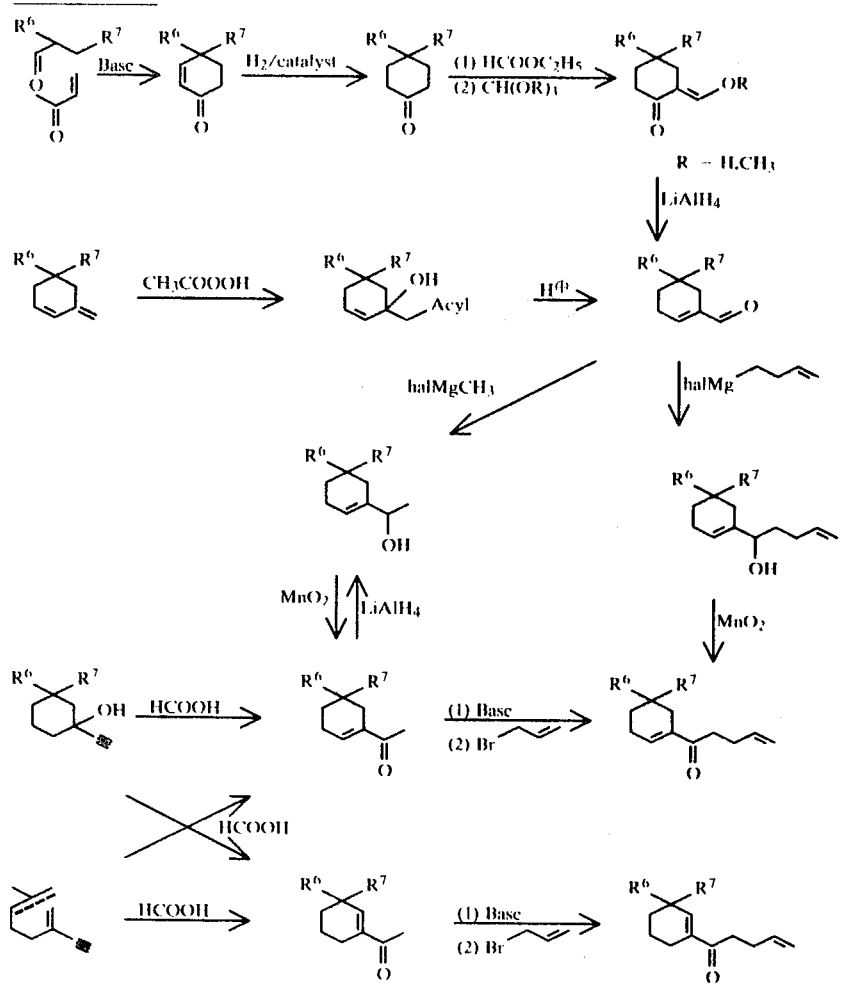
1-(3,3-Dimethyl-cyclohex-1-en-1-yl)-pent-4-en-1-one and 1-(3,3-dimethyl-cyclohex-6-en-1-yl)-pent-4-en-1-one were thus obtained.
PATHWAY IV
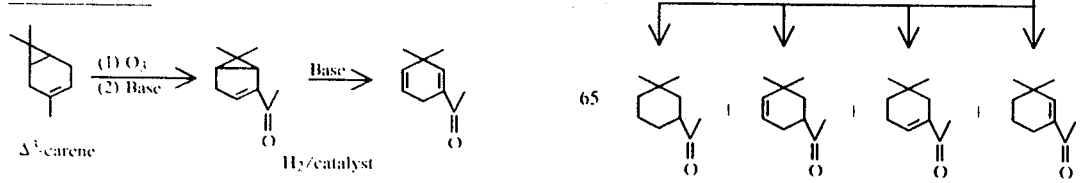

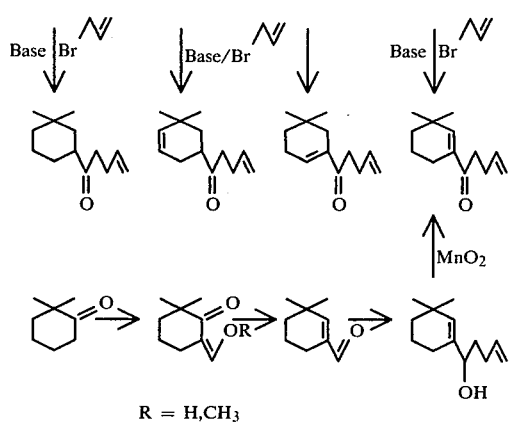

R = H,CH₃

The following compounds were thus prepared:
1-(3,3-dimethyl-cyclohexyl)-pent-4-en-1-one,
1-(3,3-dimethyl-cyclohex-4-en-1-yl)-pent-4-en-1-one,
1-(3,3-dimethyl-cyclohex-6-en-1-yl)-pent-4-en-1-one and
1-(3,3-dimethyl-cyclohex-1-en-1-yl)-pent-4-en-1-one.

1-(3,3-Dimethyl-cyclohexa-1,4-dien-1-yl)-pent-4-en-1-one,
1-(3,3-dimethyl-cyclohexa-4,6-dien-1-yl)-pent-4-en-1-one and
1-(3,3-dimethyl-cyclohexa-1,5-dien-1-yl)-pent-4-en-1-one.
were thus obtained.

PATHWAY VI

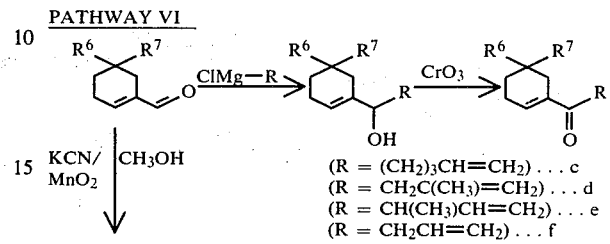

(R = (CH₂)₃CH=CH₂) ... c
(R = CH₂C(CH₃)=CH₂) ... d
(R = CH(CH₃)CH=CH₂) ... e
(R = CH₂CH=CH₂) ... f

PATHWAY V

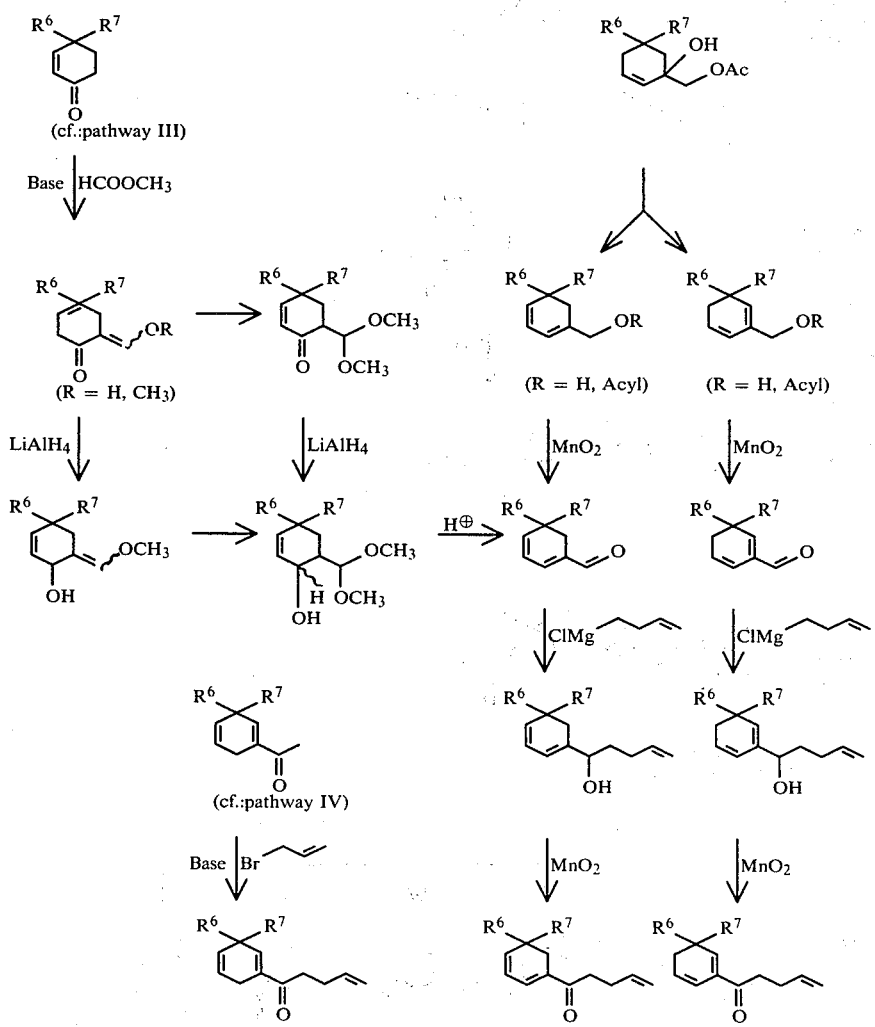

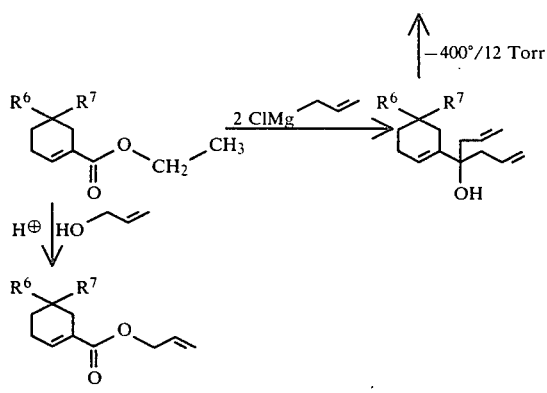
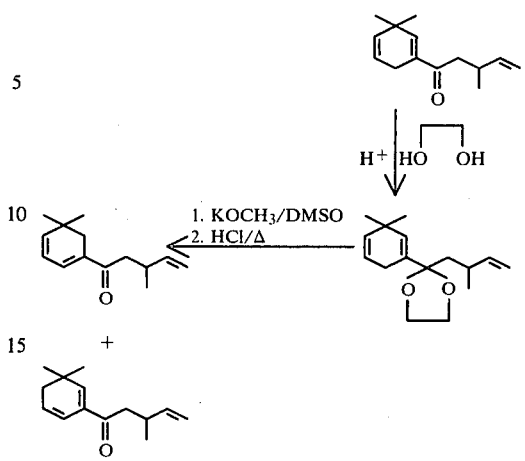

The following compounds were thus prepared:
prop-2-en-1-yl (3,3-dimethyl-cyclohex-6-en-1-yl)-carboxylate,
1-(3,3-dimethyl-cyclohex-6-en-1-yl)-hex-5-en-1-one,
1-(3,3-dimethyl-cyclohex-6-en-1-yl)-3-methyl-but-3-en-1-one,
1-(3,3-dimethyl-cyclohex-6-en-1-yl)-2-methyl-but-3-en-1-one and
1-(3,3-dimethyl-cyclohex-6-en-1-yl)-but-3-en-1-one.

1-(3,3-Dimethyl-cyclohexa-4,6-dien-1-yl)-3-methyl-pent-4-en-1-one and
1-(3,3-dimethyl-cyclohexa-1,5-dien-1-yl)-3-methyl-pent-4-en-1-one
were thus prepared.

By substituting crotyl bromide to crotyl alcohol in

PATHWAY VII

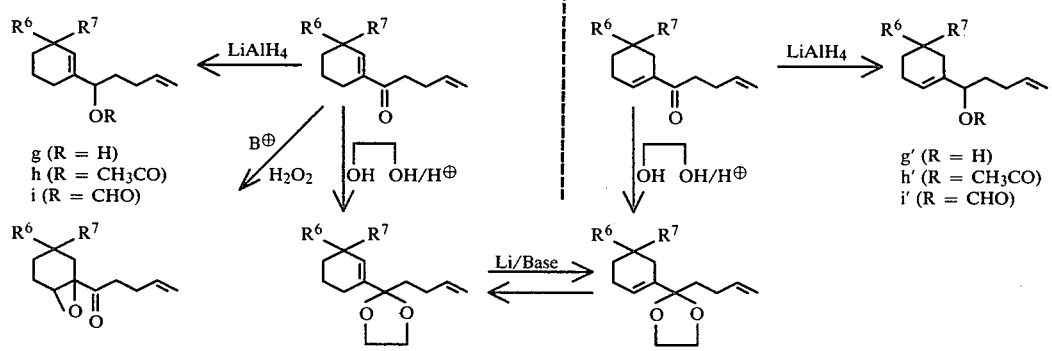

The following compounds were thus obtained:
1-(3,3-dimethyl-cyclohex-1-en-1-yl)-pent-4-en-1-yl acetate,
1-(3,3-dimethyl-cyclohex-1-en-1-yl)-pent-4-en-1-yl formate,
1-(3,3-dimethyl-cyclohex-1-en-1-yl)-1,1-ethylenedioxy-pent-4-ene,
1-(3,3-dimethyl-cyclohex-6-en-1-yl)-pent-4-en-1-yl acetate,
1-(3,3-dimethyl-cyclohex-6-en-1-yl)-pent-4-en-1-yl formate and
1-(3,3-dimethyl-cyclohex-6-en-1-yl)-1,1-ethylenedioxy-pent-4-ene.

the second step of the above reaction sequence and carrying out the following steps in much the same way as indicated above the following compounds were prepared:
1-(3,3-dimethyl-cyclohexa-4,6-dien-1-yl)-hex-4-en-1one and
1-(3,3-dimethyl-cyclohexa-1,5-dien-1-yl)-hex-4-en-1-one.

PATHWAY VII bis

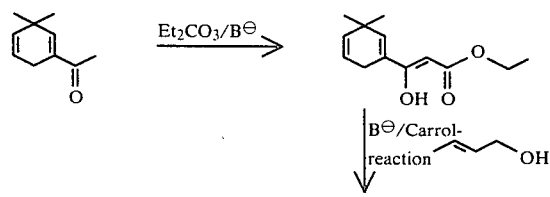

PATHWAY VIII

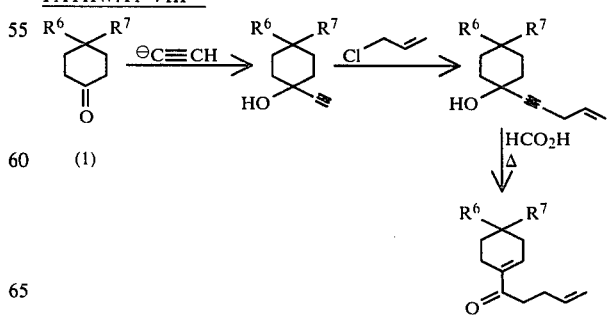

(1) cf. J. Org. Chem. 23, 1507 (1958)
J. Org. Chem. 37, 1020 (1972)

By the method indicated above 1-(4,4-dimethylcyclohex-1-en-1-yl)-pent-4-en-1-one was synthesized.

The following compounds were thus obtained:
1-(3,3-dimethyl-cyclohex-6-en-1-yl)-hex-4-en-1-one,

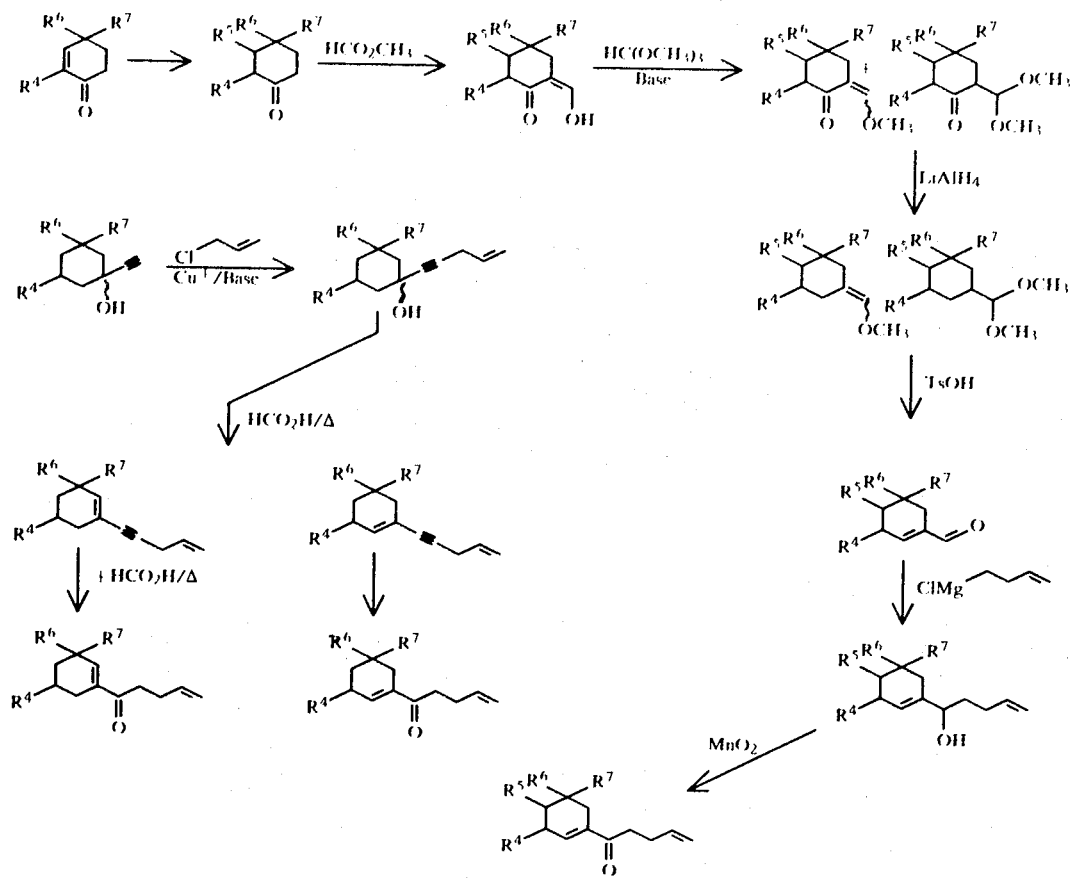

PATHWAY IX

The following compounds were thus synthesized:
1-(3,3,4-trimethyl-cyclohex-6-en-1-yl)-pent-4-en-1-one,
1-(3,3,5-trimethyl-cyclohex-6-en-1-yl)-pent-4-en-1-one and
1-(3,3,5-trimethyl-cyclohex-1-en-1-yl)-pent-4-en-1-one.

1-(3,3-dimethyl-cyclohex-1-en-1-yl)-hex-4-en-1-one,
1-(3,3-dimethyl-cyclohex-6-en-1-yl)-3-methyl-pent-4-en-1-one and
1-(3,3-dimethyl-cyclohex-1-en-1-yl)-3-methyl-pent-4-en-1-one.

The starting materials for the hereinabove given synthesis could be prepared as follows:

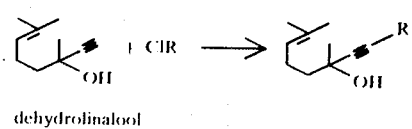

dehydrolinalool

PATHWAY X

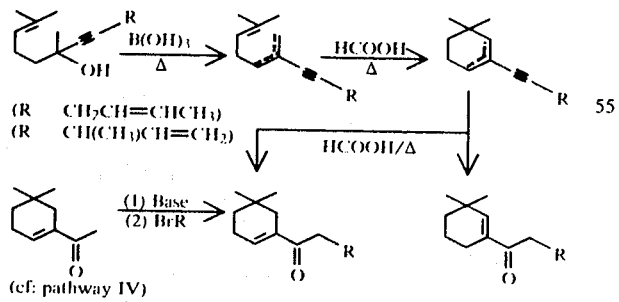

(R = CH₂CH=CHCH₃)
(R = CH(CH₃)CH=CH₂)

(cf: pathway IV)

PATHWAY XI

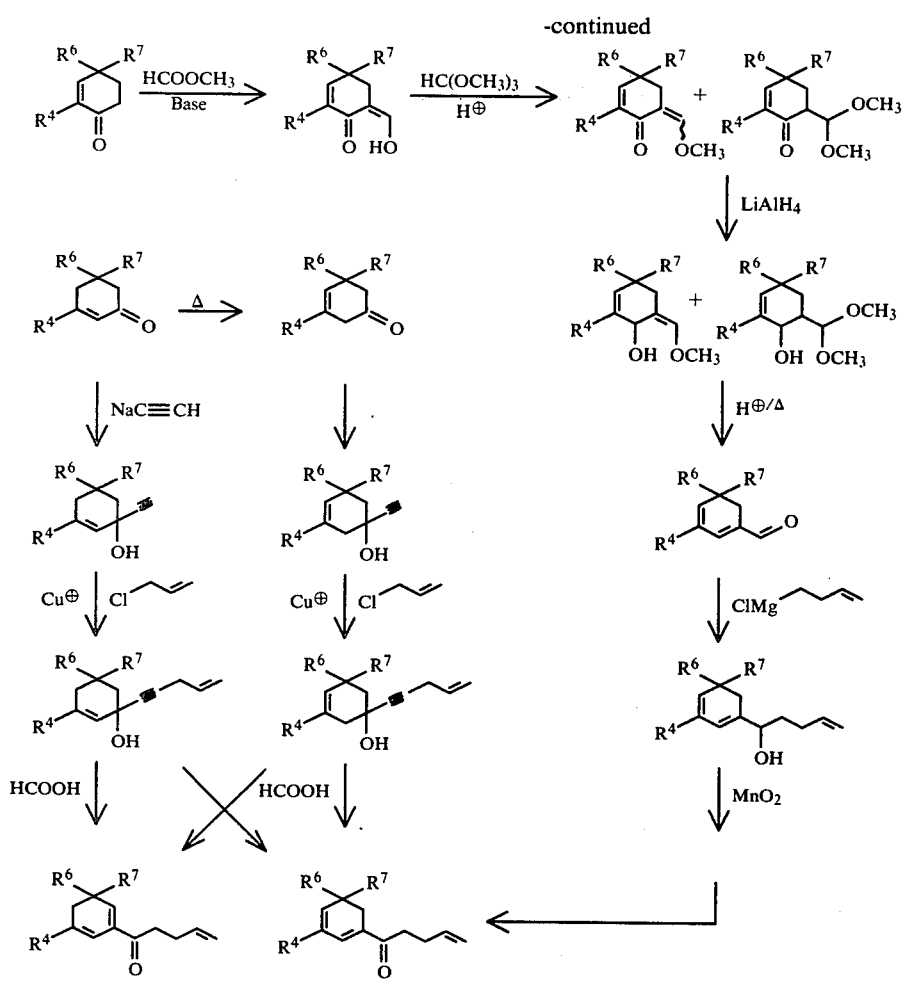

The following compounds were thus obtained:
1-(3,3,5-trimethyl-cyclohexa-1,5-dien-1-yl)-pent-4-en-1-one and
1-(3,3,5-trimethyl-cyclohexa-4,6-dien-1-yl)-pent-4-en-1-one.

PATHWAY XII

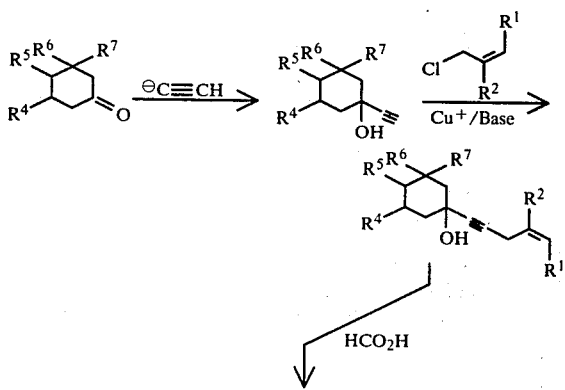

-continued

The following compounds were thus obtained:
1-(3,5-dimethyl-cyclohex-6-en-1-yl)-pent-4-en-1-one,
1-(cis-3,4-dimethyl-cyclohex-6-en-1-yl)-pent-4-en-1-one,
1-(trans-3,4-dimethyl-cyclohex-6-en-1-yl)-pent-4-en-1-one and
1-(trans-3,4-dimethyl-cyclohex-1-en-1-yl)-pent-4-en-1-one.

PATHWAY XIII

The detailed synthetic procedure followed for the preparation of the compounds of formula (I) is outlined hereinbelow. The temperatures are indicated in degrees centigrade and the abbreviations have the usual meaning.

PATHWAY XIII

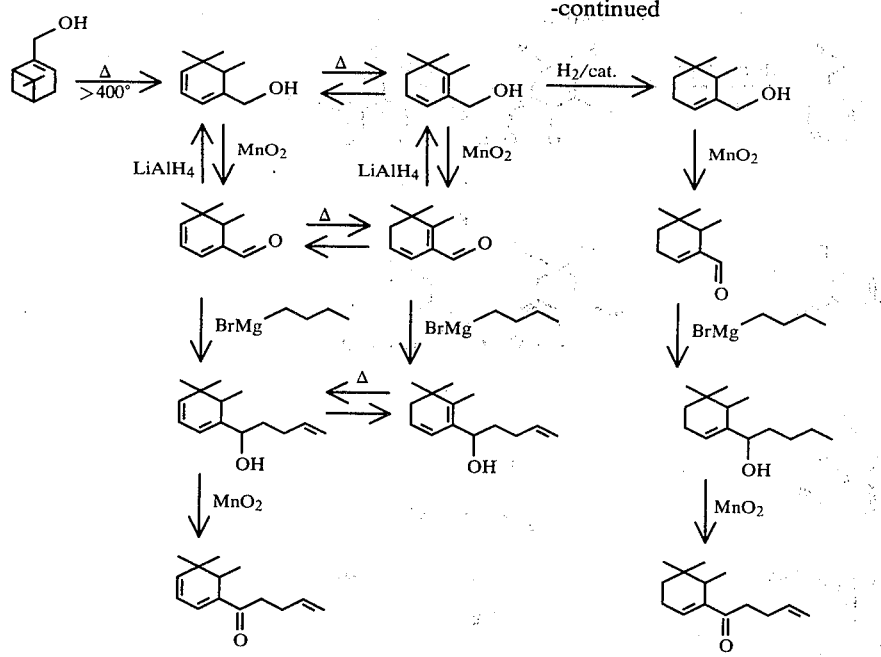

1-(2,3,3-Trimethyl-cyclohexa-4,6-dien-1-yl)-pent-4-en-1-one and
1-(2,3,3-trimethyl-cyclohex-6-en-1-yl)-pent-4-en-1-one were thus synthesized.

1-(3,3-Dimethyl-cyclohex-6-en-1-yl)-pent-4-en-1-one and
1-(3,3-dimethyl-cyclohex-1-en-1-yl)-pent-4-en-1-one
(Preparation according to pathway I)

(a) 100 g of α-dehydrolinalool were heated at 70°-5° in the presence of 30 g of B(OH)₃ at 12 Torr until no further water formation was observed. The bath temperature was then slowly increased to 160°-170° and at that temperature a mixture comprising 3-methylene-7-methyl-oct-1-yn-7-ene and 3,7-dimethyl-oct-1-yn-3,7-diene was collected by distillation in 47% yield. By using β-dehydrolinalool, instead of the corresponding α-isomer, the mixture of unsaturated olefins was obtained in 66% yield. The obtained olefins could be separated one from the other by means of fractional distillation followed by preparative v.p.c. (CARBOWAX column, CARBOWAX is a registered Trademark, of 5 m length, 130°).

(b) 2 g respectively of the olefin mixtures obtained as indicated above in 5 ml isopropanol were added dropwise to a cooled mixture of 1.1 g of KOH, 0.15 g of K₂CO₃, 0.1 g of CuCl in 5 ml methanol. After 30 minutes, to the thus obtained reaction mixture, 1.5 g of allyl chloride were slowly added. After having been left overnight under stirring, the mixture was diluted with water and petrol ether and the separated organic phase was subjected to washing, drying and evaporation. By distilling the residue in a bulb apparatus 6-methylene-10-methyl-undeca-1,10-dien-4-yne and 6-methylene-10-methyl-undeca-1,9-dien-4-yne were respectively obtained in about 80% yield in admixture with 6,10-dimethyl-undeca-1,6,10-trien-4-yne and 6,10-dimethyl-undeca-1,6,9-trien-4-yne, respectively.

(c) 100 g of the mixture of olefins obtained as indicated above were heated at 90°-100° in the presence of 200 ml of 80% formic acid. After 1½ h ⅔ of the starting material was converted into 1-(3,3-dimethyl-cyclohex-1-en-1-yl)-pent-4-en-1-yne and 1-(3,3-dimethyl-cyclohex-6-en-1-yl)-pent-4-en-1-yne. Their separation from the reaction mixture was possible by dilution of said mixture with water and petrol-ether, separation of the organic phase followed by the usual treatments of washing and drying, evaporation and distillation. The olefin mixture (77 g) was then separated into its two components by preparative v.p.c.

(d) 3 g of the olefin mixture obtained above were then heated to about 90° in the presence of 80% HCO₂H during 2½ h. After cooling, the reaction mixture was diluted with water and petrol-ether and, upon separation, the organic phase was subjected to the usual treatments. On distillation 2.8 g of a fraction having b.p. 65°-75° /12 Torr were obtained. Said fraction comprised 75% of a 2:3 mixture of 1-(3,3-dimethyl-cyclohex-1-en-1-yl)-pent-4-en-1-one (A) and 1-(3,3-dimethyl-cyclohex-6-en-1-yl)-pent-4-en-1-one (B), respectively.

(A):$n_D^{20}=1.4891$; $d_4^{20}=0.9247$
IR:3080, 1820, 1675, 1640, 990, 910 cm$^{-1}$;
NMR:1.06 (6H, 2s), 4.73-6.00 (3H, m); 6.40 (1H, m) δ ppm;
MS:M$^+$ =192 (13); m/e: 177 (6), 137 (100), 109 (85), 93 (12), 81 (32), 67 (55), 55 (58), 41 (45).

(B):$n_D^{20}=1.4879$; $d_4^{20}=0.9262$
IR: 3080, 1680, 1640, 990, 910, 820 cm$^{-1}$;
NMR:0.88 (6H, 2s), 1.32 (2H, t, J=7 Hz), 4.75-6.20 (3H, m) 6.73 (1H, m) δppm;
MS:M$^+$ =192 (7); m/e: 177 (5), 164 (3), 149 (2), 137 (100), 121 (6), 109 (45), 93 (6), 81 (13), 67 (33), 55 (28), 41 (16).

1-(3,3-Dimethyl-cyclohex-6-en-1-yl)-pent-4-en-1-one
and 1-(3,3-dimethyl-cyclohex-1-en-1-yl)-pent-4-en-1-one (Preparation according to pathway II)

3,3-Dimethyl-cyclohex-5-en-1-one, used as starting material in the hereinbelow preparation, was synthesized by known methods [cf: J. Org. Chem. 38, 3637 (1973)].

(a) A mixture of 27 g of triphenylphosphine, 15 g of 5-bromopent-1-ene in 100 ml xylene was refluxed for 40 h. After cooling to 0°–5°, the phosphonium bromide salt was separated by filtration (33 g; 100% yield) m.p. 188°–190°.

(b) 8 g of a 14% solution of butyl-lithium in diethylether were added under nitrogen within 15 min. to a suspension of 7 g of the above said phosphonium bromide in 80 ml ether. To the red resulting solution, cooled to 5°–10°, 2.1 g of 3,3-dimethyl-cyclohex-5-en-1-one in 10 ml ether, were added, whereupon, the reaction mixture was stirred for 3 h, filtered and the clear filtrate was washed with water until neutrality. On evaporation and distillation in a bulb apparatus, 1.5 g (50% yield) of (3,3-dimethyl-cyclohex-5-en-1-yliden-)-pent-4-ene were obtained.

(c) 1.5 g of the above obtained olefin were epoxidized in 20 ml CH$_2$Cl$_2$, in the presence of 1 g of sodium acetate, by 2 g of 40% peracetic acid at ca. 10°. The mixture was left under stirring for 3 h, and the organic phase was then subjected to the usual treatments. On bulb distillation 1.3 g of the epoxide of formula

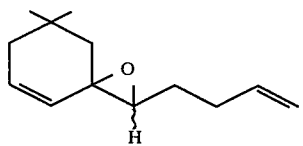

were obtained.

This product was then treated for 8 h at 100° with 0.5 g of diatomaceous earth in 10 ml dioxan. A distillation yielded 1.1 g of an oily substance which showed, on a v.p.c. analysis, to contain 30% of 1-(3,3-dimethyl-cyclohex-6-en-1-yl)-pent-4-en-1-one.

(a') A catalytic hydrogenation of 3,3-dimethyl-cyclohex-5-en-1-one was carried out according to the usual techniques in the presence of palladium on charcoal and yielded 3,3-dimethyl-cyclohexanone. The subsequent ethylination by means of acetylene in a basic medium gave 1-ethynyl-1-hydroxy-3,3-dimethyl-cyclohexane in about 50% yield.

(b') To a stirred cooled (0°–10°) mixture of 3.2 g KOH, 0.5 K$_2$CO$_3$ and 0.3 g Cu$_2$Cl$_2$ in 20 ml methanol, 4.2 g of allyl chloride in 5 ml methanol were added. The temperature was slowly increased up to 40°–50°, and the mixture was left stirring overnight. After dilution with water and petrol-ether, the organic phase was separated and evaporated to give on distillation 7.5 g (90% yield) of 1-(1-hydroxy-3,3-dimethyl-cyclohexyl)-pent-4-en-1-yne.

n$_D$=1.4899; d$_4^{20}$=0.9354

IR:3450, 3080, 2235, 1640, 990 and 910 cm$^{-1}$;

(c') 7 g of the above prepared carbinol were heated in a distillation apparatus in the presence of 2 g of H$_3$BO$_3$ at 12 Torr until no further formation of water was observed. The temperature was then slowly increased to 120°–130° and a 2:3 mixture of 1-(3,3-dimethyl-cyclohex-1-en-1-yl)-pent-4-en-1-yne and 1-(3,3-dimethyl-cyclohex-6-en-1-yl)-pent-4-en-1-yne was obtained (5.3 g; 70% yield). The subsequent conversion to the desired cyclohexenic ketones is effected according to the procedure given above (pathway I) paragraph d)

(d') A direct conversion of the carbinol prepared according to (b') into the cyclohexenic ketones was effected by treating at reflux 3 g of said carbinol with 30 ml of 80% HCO$_2$H under nitrogen during 2 h. On dilution with water and petrol ether followed by the usual treatments of the organic phase and subsequent bulb distillation at 0.1 Torr, 1.8 g of a mixture containing the two cyclohexenic ketones in a ½ proportion, respectively, were obtained.

1-(3,3-Dimethyl-cyclohex-6-en-1-yl)-pent-4-en-1-one
and 1-(3,3-dimethyl-cyclohex-1-en-1-yl)-pent-4-en-1-one (Preparation according to pathway III)

(a) A mixture of 467 g of methyl-vinyl ketone, 480 ml isobutylaldehyde, 700 ml water and 350 ml methanol was added dropwise at 60°–70° within 3 h to a mixture, kept under nitrogen, of 1000 ml water, 150 ml methanol and 25 g of KOH. Finally, the reaction mixture was stirred during 1 h at 70° and cooled then to room temperature and diluted with water. The separated organic phase was taken up with petrolether, washed with water until neutrality, dried, evaporated and fractional distilled. 325 g (yield 40%) of 4,4-dimethyl-cyclohex-2-en-1-one were obtained at b.p. 73°–6°/15 Torr.

(b) 124 g of the cyclohexenic ketone obtained as indicated above were catalytically reduced in 300 ml isopropanol in the presence of 2 g of RaNi in an atmosphere of hydrogen. 120 g of 4,4-dimethyl-cyclohexanone were thus obtained after a total hydrogen intake of 23.

IR:1720 cm$^{-1}$.

(c) 26 g of the said cyclohexanic ketone in 200 ml ether were added dropwise within 45 min at 0° to a mixture of 22 g of sodium methoxide powder, 30 g of ethylformate and 100 ml ether. The whole was left stirring overnight, then hydrolized with 600 ml iced water and acidified with 30% HCl. By extraction with petrol-ether, washing and drying of the organic extract followed by evaporation and distillation, 26 g of a formyl derivative of formula

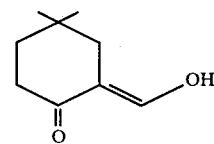

were obtained, b.p. 29°–33° /0.01 Torr (yield 75%). The subsequent etherification of the said compound was carried out by trimethylorthoformate. 15 g of the formylketone in the presence of 10.5 g of trimethylorthoformate, 20 ml of methanol and 0.1 g of toluenesulfonic acid were shortly heated at about 68° for 3–5 min, then the mixture was poured into ice. On extracting the mixture with petrol-ether, 17 g of a mixture comprising the ethers of formula

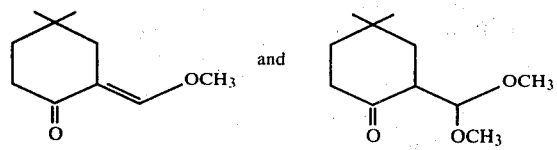

was obtained.

This mixture was used for the next reaction step without further purification.

(d) 6.0 g of the said ether mixture in 20 ml ether were added under nitrogen and vigorous stirring to a mixture of 0.8 g of LIAlH₄ in 30 ml ether and the whole was left under stirring overight. By the usual dilution with water and petrol-ether and subsequent conventional working up of the separated organic phase, 6.8 g of an oily product were obtained. This oil was refluxed with 0.3 g of toluenesulfonic acid during 1.5 h and the mixture, upon evaporation and bulb distillation of the obtained residue, gave 4.2 g of a fraction containing 78% of 1-formyl-3,3-dimethyl-cyclohex-6-ene.

(e) 1.5 g of the said formyl-derivative in 20 ml ether were added under stirring to a Grignard solution prepared from 1.3 g of methyl iodide, 1.25 g of magnesium turnings in 50 ml ether. The mixture was stirred for 2 h and finally poured into ice. The usual separation and working up of the organic phase gave on bulb distillation 1.43 g of 1-(3,3-dimethyl-cyclohex-6-en-1-yl)-1-hydroxy-ethane.

IR:3400 cm$^{-1}$;

NMR:0.91 (6H, 2s), 1.18 (3H,J=6Hz), 4.06 (1H, m), 5.53 (1H, m) δ ppm;

MS:M+ =154 (21), m/e: 139 (6), 121 (16), 85 (26), 69 (20), 43 (100).

(f) 1.2 g of the above mentioned carbinol in 50 ml petrol-ether were stirred with 20 g of MnO₂ at room temperature under a nitrogen atmosphere. The oxidation was completed in 36 h. Filtration, evaporation of the clear filtrate and bulb distillation gave 1.08 g (85%) of methyl-(3,3-dimethyl-cyclohex-6-en-1-yl)ketone.

$n_D$=1.4809; $d^{20}$=0.9309

IR:1670 and 1640 cm$^{-1}$.

(g) 10 g of the ketone prepared according to the method described above sub (f) were added to a mixture formed by the addition at 0° of 5 g of a 12% butyllithium solution to 7.3 g of di-isopropylamine in 70 ml ether. The whole was stirred for 1 h and added of 8.8 g of allyl bromide, whereupon it was left stirring overnight. The reaction mixture was then decomposed with water and the organic phase subjected to the usual treatments. On fractional distillation, 6 g of a fraction containing 20% of 1-(3,3-dimethyl-cyclohex-6-en-1-yl)-pent-4-en-1-one were obtained. The isolation of this ketone was performed by preparative v.p.c.

(h) 5 g of a 12% butyl-lithium solution in hexane were dissolved in 100 ml ether and added at 0° to a mixture of 73 g of diisopropylamine in 70 ml ether. To this mixture 10 g of methyl (3,3-dimethyl-cyclohex-1-en-1-yl) ketone were added dropwise and the whole was kept under stirring during 1 h at 0°. Then, 8.8 g of allyl bromide were added and the reaction mixture was left at room temperature overnight. The usual working up as indicated sub g) gave 5.9 g of a mixture comprising 40% of 1-(3,3-dimethyl-cyclohex-1-en-1-yl)-pent-4-en-1-one. The pure ketone was obtained by preparative v.p.c.

Methyl (3,3-dimethyl-cyclohex-1-en-1-yl) ketone used as startIng material for the above preparation was synthetized according to Z. Chem. 9, 64 (1969).

1-(3,3-Dimethyl-cyclohex-6-en-1-yl)-pent-4-en-1-one, 1-(3,3-Dimethyl-cyclohex-1-en-1-yl)-pent-4-en-1-one, 1-(3,3-Dimethyl-cyclohex-4-en-1-yl)-pent-4-en-1-one and 1-(3,3-Dimethyl-cyclohexyl-pent-4-en-1-one.

(Preparation according to pathway IV)

(a) Ozonation of Δ³-carene in methanol was performed according to Ber., 60, 1591 (1927) to give a compound of formula

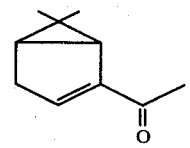

This bicyclic ketone was refluxed with some drops of 25% KOH in 10 times its volume of methanol. After 1½ h the product was worked up with water and ether and the separated organic phase gave on distillation (3,3-dimethyl-cyclohexa-,1,4-dien-1-yl) methyl ketone in 65% yield.

m.p. 27°-30°; $n_D$=1.4886; $d^{20}$=0.9493

IR: 1670, 1630, 1560, 720 cm$^{-1}$;

UV (EtOH): λ: 220, 240 and 310 nm.

(b) A subsequent catalytic reduction, in the presence of Pd over charcoal, carried out on 15 g of the above ketone gave a 31:35: 17:17 mixture of the following ketones

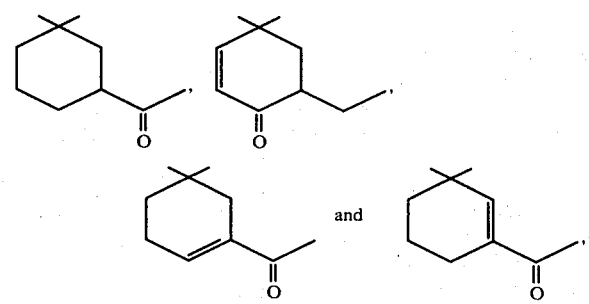

respectively These ketones could be separated one from the others by preparative v.p.c.

(c) 1-(3,3-dimethyl-cyclohex-4-en-1-yl)-pent-4-en-1-one and 1-(3,3-dimethyl-cyclohexyl)-pent-4-en-1-one were obtained together with 1-(3,3-dimethyl-cyclohex-6-en-1-yl)-pent-4-en-1-one and 1-(3,3-dimethyl-cyclohex-1-en-1-yl)-pent-4-en-1-one, by treatment of the corresponding ketones with allyl bromide in the presence of lithium-diisopropylamide as basic reagent according to the same procedure as that described in pathway II, paragraph (h). Whenever the mixtures of ketones were used as starting material, the final products were separated one from the others by preparative v.p.c. The compounds had the following analytical data:

1-(3,3-dimethyl-cyclohexyl)-pent-4-en-1-one $n_D$=1.4749; $d^{20}$=0.9226

IR: 3080, 1705, 1640, 990 and 910 cm$^{-1}$;
NMR: 0.9 (6H, 2s), 4.72–6.1 (3H, m) δ ppm;
MS: M$^+$=194 (3); m/e: 179 (2), 139 (27), 117 (60), 111 (100), 69 (92), 55 (85), 41 (40).

1-(3,3-dimethyl-cyclohex-4-en-1-yl)-pent-4-en-1-one n$_D$=1.4788; d$^{20}$=0.9212
IR: 3080, 1710, 1645, 990, 910 and 722 cm$^{-1}$;
NMR: 1.02 (6H, 2s), 4.76–6.1 (3H, m), 5.41 (2H, m) δ ppm;
MS: M$^+$=192 (5); m/e: 177 (7), 109 (45), 83 (82), 67 (44), 55 (100), 41 (55).

1-(3,3-Dimethyl-cyclohexa-1,4-dien-1-yl)-pent-4-en-1-one 1-(3,3-Dimethyl-cyclohexa-4,6-dien-1-yl)-pent-4-en-1-one 1-(3,3-Dimethyl-cyclohexa-1,5-dien-1-yl)-pent-4-en-1-one (Preparation according to pathway V)

(a) 52 g of sodium methoxide were added at 0°–5° in a nitrogen atmosphere to a mixture of 71 g of ethylformate in 700 ml ether. To the resulting mixture, kept under stirring for 20 min, 60 g of 4,4-dimethyl-cyclohex-2-en-,1-one were added dropwise and the whole was left under stirring overnight and poured then into ice. The ethereal phase was separated, and the aqueous liquor was washed with ether and acidified with HCl. The hydroxy-ketone of formula

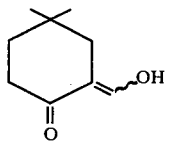

did separate and was taken up, in ether, washed with water, neutralised with NaHCO$_3$ and fractional distilled. 63.1 g of the said hydroxy-ketone having b.p. 40°–45°/0.1 Torr (yield 87%) were thus obtained. n$_D$=1.5231; d$_4^{20}$=1.036 (b) The said hydroxy-ketone was converted into its mono- and dimethyl ether derivatives in accordance with the procedure give in pathway III, paragraph c).

mono-methoxy ketone:
n$_D$=1.5167; d$^{20}$=1.035
IR: 1680, 1625, 1590 cm$^{-1}$;
di-methoxy-ketone:
n$_D$=1.4821; d$_4^{20}$=1.033
IR: 1680, 770, 710 cm$^{-1}$.

(c) 26 g of a 7:3 mixture of the mono- and di-methoxy ketones prepared as indicated above in 50 ml ether were added under nitrogen and vigourous stirring to a suspension of 5.5 g of LiAlH$_4$ in 200 ml of ether at 0°–10°. After having been left under stirring overnight, the mixture was worked up as usual and extracted with ether. 18.3 g of a mixtUre of the corresponding carbinols were thus obtained under a vacuum of 0.01 Torr.
IR: 3400, 725 cm$^{-1}$;

This mixture was directly treated at the boiling for 2 h with 0.5 g of toluenesulfonic acid in 250 ml toluene. On bulb distillation, 14 g of a product comprising 50% of 3,3-dimethyl-1-formyl-cyclohexa-4,6-diene were obtained. A purification was afforded by "Girard" reagents and enabled to separate 7.8 g (yield 35%) of the pure aldehyde. n$_D$=1.5089; d$^{20}$=0.9672
IR: 3060, 2620, 1675, 1575 and 704 cm$^{-1}$;

(d) 1.5 g of the above prepared aldehyde in 50 ml diethylether were added under nitrogen and stirring to a Grignard solution prepared from 0.3 g of magnesium turnings and 1.7 g of 1-bromo-but-3-ene in 20 ml ether. Then, the reaction mixture was refluxed for 1 h and after cooling worked up as usual. On bulb distillation (100°/0.01 Torr) 1.5 g (76% yield) of 1-(3,3-dimethyl-cyclohexa-4,6-dien-1-yl)-1-hydroxy-pent-4-ene were obtained.
n$_D$=1.4999; d$^{20}$=0.9754
IR: 3450, 3080, 1640, 990, 910 and 725 cm$^{-1}$.

(e) 1 g of said carbinol was oxidised by means of 12 g of MnO$_2$ in 200 ml petrol-ether under nitrogen. The whole reaction was completed after 24 h. On bulb distillation, 0.85 g of pure 1-(3,3-dimethyl-cyclohexa-4,6-dien-1-yl)-pent-4-en-1-one were obtained at 0.1 Torr.
n$_D$=1.5009; d$^{20}$=0.9309
IR: 3080, 1670, 1640, 1580, 990 and 910 cm$^{-1}$;
NMR: 1.01 (6H, 2s), 4.75–6.1 (3H, m), 5.88 (2H, m) and 6.76 (1H, m) δ ppm;
MS: M$^+$=190 (20); m/e: 175 (30), 148 (16), 135 (90), 119 (100), 109 (80), 91 (80), 55 (90), 41 (40).

(f) 1-Methylene-3,3-dimethyl-cyclohex-5-ene was prepared by the procedure given in Bull. Soc. Chim. France 4170 (1972) starting from isophorol. Its conversion into (1-hydroxy-3,3-dimethyl-cyclohex-5-en-1-yl)-methyl acetate was performed as follows:

237 g of the hydrocarbon were dissolved in 300 ml CH$_2$Cl$_2$ and treated with 260 g of anhydrous sodium carbonate. To this mixture, 400 g of 40% peracetic acid was added, followed by 10 g of Na$_2$CO$_3$ while keeping the reaction temperaure at about 20°. The following working up in water, separation of the organic phase, evaporation and preparative v.p.c. on the residue gave the pure desired hydroxy-acetate.
n$_D$=1.4741; d$^{20}$=1.031
IR: 3450, 1740, 732 cm$^{-1}$.

(g) The residue as directly obtained above, was dissolved in 1000 ml toluene and refluxed in the presence of 3 g of toluenesulfonic acid in a water separator. After 1 h, a 1:1 mixture comprising (3,3-dimethyl-cyclohexa-1,5-diene-1-yl)-methyl acetate and (3,3-dimethyl-cyclohexa-4,6-dien-1-yl)-methyl acetate was obtained. A saponification and subsequent oxidation by means of MnO$_2$ enabled to obtain 1-formyl-3,3-dimethyl-cyclohexa-4,6-diene and 1-formyl-3,3-dimethyl-cyclohexa-1,5-diene as a 1:2 mixture. n$_D$=1.5022; d$^{20}$=0.9705.

(h) The obtained aldehydic mixture was directly subjected to a Grignard reaction with but-3-enyl-magnesium chloride in order to give the corresponding carbinols according to the procedure described above—cf. paragraph (d)—and these latters were converted into the desired ketones by means of MnO$_2$. 1-(3,3-dimethyl-cyclohexa-1,5-dien-1-yl)-pent-4-en-1-one showed the following NMR data:
1.1 (6H, 2s),, 2.3 (2H, m), 4.8–6.1 (3H, m), 5.65 (2H, m) and 6.32 (1H, m) δ ppm.

The corresponding 1,4-diene derivative, 1-(3,3-dimethyl-cyclohexa-1,4-dien-1-yl)-pent-4-en-1-one, was obtained from (3,3-dimethyl-cyclohexa-1,4-dien-1-yl) methyl ketone and allyl bromide according to the procedure described in pathway III, paragraph h).
n$_D$=1.4981; d$^{20}$=0.9759
IR: 3070, 1675, 1625 and 722 cm$^{-1}$;

NMR: 1.11 (6H, 2s), 4.8–6.1 (3H, m), 5.5 (2H, m) 6.47 (1H, m) δ ppm;

MS: M+ =190 (1); m/e: 175 (60), 135 (20), 119 (100), 107 (40), 91 (55), 55 (65), 43 (25).

Prop-2-en-1-yl (3,3-dimethyl-cyclohex-6-en-1-yl)-carboxylate, 1-(3,3-dimethyl-cyclohex-6-en-1-yl)-hex-5-en-1-one, 1-(3,3-dimethyl-cyclohex-6-en-1-yl)-3-methyl-but-3-en-1-one, 1-(3,3-dimethyl-cyclohex-6-en-1-yl)-2-methyl-but-3-en-1-one and 1-(3,3-dimethyl-cyclohex-6-en-1-yl)-but-3-en-1-one.

Preparation according to pathway VI)

(a) 1-Formyl-3,3-dimethyl-cyclohex-6-ene—cf. pathway III—was converted into the corresponding hydroxy-alkyl derivatives of formula

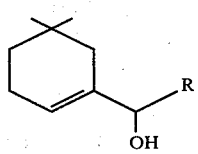 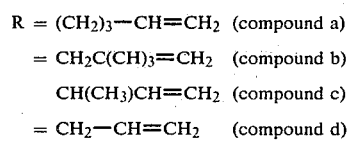

R = (CH₂)₃—CH=CH₂ (compound a)
= CH₂C(CH₃)=CH₂ (compound b)
= CH(CH₃)CH=CH₂ (compound c)
= CH₂—CH=CH₂ (compound d)

by a Grignard reaction.

The analytical data were as follows:

Compound a $n_D$=1.4832; $d^{20}$=0.9143
IR: 3450, 3075, 1640, 990 and 910 cm⁻¹.

Compound b $n_D$=1.4858; $d^{20}$=0.9198
IR: 3450, 3075, 1645, and 885 cm⁻¹.

Compound c $n_D$=1.4845; $d^{20}$=0.9198
IR: 3400, 3075, 1645, 990 and 910 cm⁻¹.

Compound d $n_D$=1.4853; $d^{20}$=0.9243
IR: 3450, 3075, 1640, 990 and 910 cm⁻¹.

(b) The subsequent oxidation was effected as exemplified hereinbelow:

1 part by weight of the carbinols in 10 times their volume of toluene was mixed at 10°–15° under nitrogen with 15 parts of Na₂Cr₂O₇, 4 parts of concentrated H₂SO₄ and 5 parts of water. After 12 h stirring, the separated organic phase was subjected to the usual treatments. On distillation the pure desired ketones were obtained.

1-(3,3-Dimethyl-cyclohex-6-en-1-yl)-hex-5-en-1-one $n_D$=1.4868; $d^{20}$=0.9226
IR: 3075, 1665, 1640, 990 and 910 cm⁻¹;
NMR: 0.91 (6H, 2s), 4.75–6.0 (3H, m) δ ppm;
MS: M+ =206 (15); m/e: 152 (72), 137 (90), 109 (100), 67 (60), 53 (40), 41 (70).

1-(3,3-Dimethyl-cyclohex-6-en-1-yl)-3-methyl-but-3-en-1-one $n_D$=1.4883; $d^{20}$=9.9461
IR: 3080, 1665, 1640, 885 cm⁻¹;

NMR: 0.91 (6H, 2s), 132 (2H, t, J=5Hz), 1.72 (3H, s), 3.26 (2H, m), 4.66 and 4.8 (2H, 2m), 6.78 (1H, m) δ ppm.

MS: M+ =192 (1); m/e: 177 (3), 137 (100), 121 (10), 109 (40), 81 (12), 87 (36), 55 (28), 41 (18).

1-(3,3-Dimethyl-cyclohex-6-en-1-yl)-2-methyl-but-3-en-1-one $n_D$=1.4822; $d^{20}$=0.9358
IR: 3075, 1665, 1640, 990 and 910 cm⁻¹;
NMR: 0.91 (6H, 2s), 1.16 (3H, d, J=7Hz), 3,78 (1H, m) 4.76–6.1 (3H, m), 6.79 (1H, m) δ ppm;
MS: M+ =192 (1); m/e: 177 (2), 137 (100), 124 (3), 109 (30), 81 (12), 67 (30), 31 (15).

1-(3,3-Dimethyl-cyclohex-6-en-1-yl)-but-3-en-1-one $n_D$=1.4828; $d^{20}$=0.9387
IR: 3080, 1668, 1640, 990 and 910 cm⁻¹;
NMR: 0.92 (6H, 2s), 1.36 (2H, t, J=6Hz), 3.32 (2H, d, J=5Hz), 4.8–6.1 (3H, m), 6.78 (1H, m) δ ppm;
MS: M+ =178 (3); m/e: 165 (12), 137 (100), 109 (40), 67 (44), 41 (26).

This latter compound could be synthesized also from 1-formyl-3,3-dimethyl-cyclohex-6-ene via ethyl (3,3-dimethylcyclohex-6-en)-carboxylate. 1.8 g of this ester, prepared according to J. Am. Chem. Soc., 90, 5616 (1968), was subjected to a Grignard reaction and converted by means of allyl-magnesium bromide to the carbinol of formula

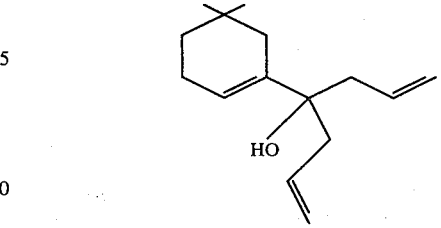

having $n_D$=1.4928; $d^{20}$=0.9276
IR: 3450, 3080, 1640, 990 and 910 cm⁻¹.

On pyrolysing 5 g of the above said carbinol at about 440° under 12 Torr there were obtained 3.5 g of a mixture comprising 65% of 1-(3,3-dimethyl-cyclohex-6-en-1-yl)-but-3-en-1-one.

Prop-2-en-1-yl (3,3-dimethyl-cyclohex-6-en-1-yl)-carboxylate was prepared from ethyl (3,3-dimethyl-cyclohex-6-en-1-yl)-carboxylate as follows:

3.8 g of this latter ester were refluxed with 44 ml of a 1:1 solution of water and methanol overnight. The resulting solution was taken up with petrol-ether and the aqueous phase was evaporated to dryness. The solid residue was refluxed in 50 ml acetone in the presence of 3.1 g of allyl bromide under nitrogen during 2 h. After filtration of the reaction mixture the clear filtrate was evaporated and the obtained residue distilled to give 3.1 g (80% yield) of the desired ester.

B.p. 70°–75°/0.1 Torr; $n_D$=1.4789; $d^{20}$=0.9811
IR: 3080, 1715, 1640, 990 and 915 cm⁻¹;
NMR: 0.9 (6H, 2s); 1.32 (2H, t, J=5 Hz), 2.1 (2H, m), 4.45–6.2 (3H, m), 6.86 (1H, m) δ ppm;
MS: M+ =194 (20); m/e: 179 (10), 153 (40), 137 (60), 167 (48), 93 (52), 67 (40), 41 (100).

1-(3,3-Dimethyl-cyclohex-1-en-1-yl)-pent-4-en-1-yl acetate, 1-(3,3-dimethyl-cyclohex-1-en-1-yl)-pent-4-en-1-yl formate, 1-(3,3-dimethyl-cyclohex-1-en-1-yl)-1,1-ethylenedioxy-pent-4-ene, 1-(3,3-dimethyl-cyclohex-6-en-1-yl)-pent-4-en-1-yl acetate, 1-(3,3-dimethyl-cyclohex-6-en-1-yl)-pent-4-en-1-yl formate, 1-(3,3-dimethyl-cyclohex-6-en-1-yl)-1,1-ethylenedioxy-pent-4-ene.

(Preparation according to pathway VII)

(a) 15 g of 1-(3,3-dimethyl-cyclohex-1-en-1-yl)-pent-4-en-1-one, respectively 1-(3,3-dimethyl-cyclohex-6-en-1-yl)-pent-4-en-1-one, in 50 ml ether were reduced by means of LiAlH$_4$ (2.2 g) by keeping the reagents under stirring for 1 h. The corresponding carbinols were obtained by fractional distillation.

(b) The conversion into the corresponding acetates was effected by the usual acetylation methods by means of acetic anhydride:

1-(3,3-Dimethyl-cyclohex-1-en1-yl)-pent-4-en-1-yl acetate $n_D = 1.4648$; $d^{20} = 0.9374$
IR: 3080, 1730, 1635, 1230, 990 and 910 cm$^{-1}$;
NMR: 0.99 (6H, 2s), 1.98 (3H, s), 4.8–6.1 (3H, m), 5.32 (1H, m) δ ppm;
MS: M$^+$ = 236 (0.1); m/e: 194 (10), 176 (6), 161 (15), 135 (30), 107 (40), 93 (25), 81 (32), 55 (35), 43 (100).

1-(3,3-Dimethyl-cyclohex-6-en-1-yl)-pent-4-en-1-yl acetate $n_D = 1.4681$; $d^{20} = 0.9592$
IR: 3080, 1740, 1640, 990 and 910 cm$^{-1}$;
NMR: 0.91 and 0.92 (6H, 2s), 132 (2H, t, J≃5 Hz), 1.75 (2H, 1m), 1.98 (3H, s), 2.01 (2H, m), 4.8–6.1 (3H, m), 5.56 (1H, m) δ ppm.
MS: M$^+$ = 236 (0.1); m/e: 194 (14), 176 (12), 135 (40), 107 (26), 93 (30), 79 (32), 43 (100).

(c) The conversion of the prepared carbinols into their corresponding formates is effected by reacting them with 5 times their volumes of 100% HCO$_2$H, in the presence of molecular sieves (2 volumes) and toluene (5 volumes) at room temperature. Reaction time: 12 h. The purification of the thus obtained ester was achieved by column chromatography on silica gel with a 9:1 hexane: ether mixture as diluent.

1-(3,3-Dimethyl-cyclohex-1-en-1-yl)-pent-4-en-1-yl formate $n_D = 1.4704$; $d^{20} = 0.9486$
IR: 3075, 1725, 1645, 1175, 990 and 910 cm$^{-1}$;
NMR: 0.98 (6H, 2s), 4.8–6.1 (3H, m), 5.4 (H, m), 7.9 (1H, s) δ ppm;
MS: M$^+$ = 222 (0.1); m/e: 208 (1), 177 (15), 161 (35), 135 (60), 109 (70), 93 (45), 81 (55), 69 (65), 55 (90), 41 (100).

1-(3,3-Dimethyl-cyclohex-6-en-1-yl)-pent-4-en-1-yl formate $n_D = 1.4759$; $d^{20} = 0.9515$ IR: 3080, 1730, 1640, 1180, 990 and 910 cm$^{-1}$; NMR: 0.92 and 0.94 (6H, 2s), 4.8–6.1 (3H, m), 5.66 (1H, m), 7.92 (1H, s) δ ppm;
MS: M$^+$ = 222 (1); m/e: 207 (1), 192 (2), 176 (24), 161 (24), 135 (98), 107 (60), 79 (75), 69 (50), 41 (100).

(d) The ethylene ketals derivatives were prepared from the corresponding ketones by reacting them with ethyleneglycol in benzene in the presence of toluenesulfonic acid. Reaction times: 3–4 h.

1-(3,3-Dimethyl-cyclohex-1-en-1-yl)-1,1-ethylenedioxy-pent-4-ene $n_D = 1.4761$; $d^{20} = 0.9607$
IR: 3080, 1640, 1190, 1040, 990 and 910 cm$^{-1}$;
NMR: 1.0 (6H, 2s), 3.78 (4H, m), 4.72–6.1 (3H, m), 5.5 (1H, m), δ ppm
MS: M$^+$ = 236 (0.1); m/e: 181 (100), 166 (1), 137 (2), 127 (20), 109 (10), 73 (10), 55 (12).

1-(3,3-Dimethyl-cyclohex-6-en-1-yl)-1,1-ethylenedioxy-pent-4-ene $n_D = 1.4810$; $d^{20} = 0.9677$
IR: 3080, 1640, 1190, 1040, 990 and 910 cm$^{-1}$;
NMR: 0.9 (6H, 2s), 38 (4H, m), 4.75–6.1 (3H, m), 5.75 (1H, m) δ ppm;
MS: M$^+$ = 236 (0.1); m/e: 221 (1), 207 (1), 181 (100), 137 (15), 127 (20), 109 (10), 91 (7), 55 (20), 41 (10).

1-(3,3-Dimethyl-cyclohexa-4,6-dien-1-yl)-3-methyl-pent-4-en-1-one and 1-(3,3-dimethyl-cyclohexa-1,5-dien-1-yl)-3-methyl-pent-4-en-1-one (Preparation according to pathway VII bis)

(a) (3,3-Dimethyl-cyclohexa-1,4-dien-1-yl) methyl ketone used as starting material was obtained from Δ$^3$-carene as indicated above (cf. Pathway IV).

180 g (1.5 M) of ethyl carbonate together with 27 g (0.5 M) of sodium methoxide were poured in a distillation vessel and at 55° allowed to react with a mixture of 0.25 M (37.5 g) of the above said methyl ketone and 0.5 M of ethyl carbonate. This latter mixture was added dropwise under vigorous stirring within a period of approximately 2–3 hours, whereupon the volatile fractions were taken off under vacuum (80 Torr) at 60°. The residue was then cooled, mixed with 50 ml acetic acid and 400 ml ice water, then extracted with ethyl acetate. The organic phase was neutralised with a NaHCO$_3$ aqueous solution, dried over Na$_2$SO$_4$ and distilled to give a compound having b.p. 75°–80°/0.01 Torr; $n_D = 4960$; $d^{20} = 0.8292$ (b) 5 g of the ester obtained under letter (a) above were slowly heated to 120° with 1.44 g of crotyl alcohol and 0.5 g aluminum isopropylate during ca. 2h. The temperature was then alowed to increase to 200° and 3.7 g of 1-(3,3-dimethyl-cyclohexa-1,4-dien-1-yl)-3-methyl-pent-4-en-1-one were thus obtained by distillation.

(c) By treating the obtained ketone with 1.5 equivalents of ethylene-glycol in the presence of p-toluene-sulphonic acid in benzene the corresponding ketal was obtained in good yields. $n_D = 1.4831$; $d^{20} = 0.9702$ (d) The ketal was isomerized by treating it with catalytic amounts of potassium methoxide in dimethylsulfoxide at about 100°–120°, whereupon a saponification with HCl gave the desired cyclohexadienic ketones under the form of a mixture of ca. 2:1 of 1-(3,3-dimethyl-cyclohexa-4,6-dien-1-yl)-3-methyl-pent-4-en-1-one and 1-(3,3-dimethyl-cyclohexa-1,5-dien-1-yl)-3-methyl-pent-4-en-1-one.

B.p. 110°/0.01 Torr; $n_D$=1.5039; $d^{20}$=0.9271

IR: 3080, 1650, 1560, 990, 910 and 738

NMR: 1.0 and 1.08 (2 s, 6H); 1.02 (3H, d, J≃6.5 cps); 2.0–2.85 (5H); 4.7–6.0 (3H, m); 5.7–6.8 (3H) δ ppm;

MS: M+ =204 (12); m/e: 189 (12), 135 (100), 119 (80), 107 (36), 91 (70), 69 (35), 55 (70).

1-(3,3-Dimethyl-cyclohexa-4,6-dien-1-yl)-hex-4-en-1-one and 1-(3,3-Dimethyl-cyclohexa-1,5-dien-1-yl)hex-4-en-1-one 11.1 g of the ester prepared as described above under letter (a) were mixed during 30 min. at room temperature with 3 g of sodium methoxide in 80 ml of dimethylformamide, whereupon 7 g of crotyl bromide were added dropwise to the reaction mixture which was then left under stirring overnight. 100 ml of a 1N NaOH solution and 150 ml of ethanol were then added to the reaction mixture which was thus left under stirring for 12 h. A neutralisation with a 10% HCl solution, extraction with ether, followed by the usual working up gave 9.1 g of 1-(3,3-dimethyl-cyclohexa-1,4-dien-1-yl)-hex-4-en-1-one.

The subsequent ketalisation and conversion into the desired cyclohexadienic ketones can be effected in accordance with the same procedure as that indicated above under letter (c) and (d). The products were obtained as a ca. 2:1 mixture of 1-(3,3-dimethyl-cyclohexa-4,6-dien-1-yl)-hex-4-en-1-one and 1-(3,3-dimethyl-cyclohexa-1,5-dien-1-yl)-hex-4-en-1-one respectively.

$n_D$=1.5071; $d^{20}$=0.9360;

IR: 1670, 1570, 965, 735 cm$^{-1}$;

NMR: 1.0 and 1.09 (6H, 2s); 1.5 (3H, d, J≃6.5 cps); 2.0–2.8 (6H); 5.25–6.8 (5H) δ ppm;

MS: M+ =204 (92); m/e: 189 (40), 135 (100), 119 (94), 107 (52), 91 (82), 69 (60), 55 (75), 41 (60).

1-(4,4-Dimethyl-cyclohex-1-en-1-yl)-pent-4-en-1-one (Preparation according to pathway VIII)

(a) 1-Ethynyl-4,4-dimethylcyclohexanol was prepared according to the procedure described in J. Chem. Soc. 79, 5886 (1957).

(b) The conversion of the obtained acetylenic carbinol into its corresponding enyne occurred by reacting it with alkyl chloride in accordance with the method described in pathway I, paragraph (b) in 78% yield.

$n_D$=1.4919; $d^{20}$=0.9378

IR: 3400, 3080, 2290, 1640, 990 and 910 cm$^{-1}$;

NMR: 0.96 (6H, 2s), 3.0 (2H, m), 4.95–6.1 (3H, m) δ ppm

MS: M+ =192 (3); m/e: 177 (7), 159 (8), 122 (100), 121 (90), 71 (65), 43 (55).

(c) The subsequent formation of the derived ketone occurs by treating the product obtained sub (b) for 2–3 h with twice its volume of 80% formic acid under the Rupe's reaction conditions.

Yield 68%.

$n_D$=1.4881; $d^{20}$=0.9298;

IR: 3080, 1670, 1640, 990 and 910 cm$^{-1}$;

NMR: 0.92 (6H, 2s), 1.4 (3H, t, J=6 Hz), 4.75–6.1 (3H, m), 6.69 (1H, m), δ ppm;

MS: M+ =192 (3); m/e: 177 (2), 137 (100), 109 (20), 81 (50), 69 (25), 55 (36), 41 (30).

1-(3,3,4-Trimethyl-cyclohex-6-en-1-yl)-pent-4-en-1-one, 1-(3,3,5-trimethyl-cyclohex-6-en-1-yl)-pent-4-en-1-one and 1-(3,3,5-trimethyl-cyclohex-1-en-1-yl)-pent-4-en-1-one.

(Preparation according to pathway IX)

The starting cyclohexanic ketones, i.e. 2,4,4-cyclohexanone, is a known compound—cf. Ber. 94, 2486 (1961).

(a) 109 g of CuCl were added in small portions to a Grignard solution prepared from 26.4 g of magnesium turnings and 156.2 g of methyliodide in 200 ml diethylether under a nitrogen atmosphere. To the reaction mixture there were then added 124 g of 4,4-dimethyl-cyclohex-2-en-1-one in ether solution and the whole was refluxed for 2 h. The mixture was then hydrolysed with a saturated aqueous solution of ammonium chloride and subjected to the usual treatments to afford on distillation 88 g (63% yield) of 3,4,4-trimethyl-cyclohexanone; B.p. 80°–85°/12 Torr.

(b) To a cooled mixture of 46 g of methyl formate in 200 ml ether kept under nitrogen, there were subsequently added 34 g of sodium methoxide and 43 g of the above prepared ketone in 100 ml ether. The temperature of the mixture was kept at about 5°–10° during the whole addition. The mixture was left overnight under stirring and poured then into crushed ice before extracting it with ether. The usual treatments gave 30 g (65% yield) of the carbinol of formula

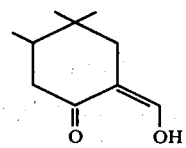

(c) The corresponding keto ether was obtained by reacting the said carbinol with methylorthoformate according to the procedure given in pathway IV.

(d) The subsequent reduction to the corresponding saturated ethers is performed by LiAlH$_4$ in ether solution at a temperature of 0°–5°. From 7.7 g of keto ether there were obtained 6.6 g of hydroxy-ether.

(e) 4 g of the said hydroxy-ether were refluxed with 0.2 g of toluenesulfonic acid in 75 ml of toluene. 2.7 g of 1-formyl-3,3,4-trimethyl-cyclohex-6-ene were thus obtained. $n_D$=1.4849; $d^{20}$=0.9484.

(f) The formation of 1-(3,3,4-trimethyl-cyclohex-6-en-1-yl)-pent-4-en-1-ol by means of but-4-en-1-yl magnesium chloride addition and subsequent oxidation by means of MnO$_2$ were performed in accordance with pathway V, paragraph (e), to give:

1-(3,3,4-trimethyl-cyclohex-6-en-1-yl)-pent-4-en-1-one $n_D$=1.4896; $d^{20}$=0.9311

IR: 3080, 1670, 1640, 990 and 910 cm$^{-1}$;

NMR: 0.9 (3H, d,J=6 Hz), 0.78 and 0.99 (6H, 2s), 4.76–6.1 (3H, m), 6.7 (1H, m) δ ppm;

MS: M+ =206 (10); m/e: 191 (5), 151 (100), 123 (22), 95 (12), 81 (35), 70 (20), 55 (35), 41 (20).

By an analogous method starting from 2,4,4-trimethyl-cyclohexanone there was obtained 1-(3,3,5-trimethyl-cyclohex-6-en-1-yl)-pent-4-en-1-one:

$n_D$=1.4853; $d^{20}$=0.9170

IR: 3080, 1670, 1645, 990 and 910 cm$^{-1}$;

NMR: 1.11 (3H, d, J=7 Hz), 0.82 and 1.03 (6H, 1s), 4.75–6.1 (3H, m), 6.5 (1H, m) δ ppm;

MS: M+ =206 (45); m/e: 191 (10), 165 (25), 151 (100), 123 (95), 81 (60), 67 (60), 55 (65), 41 (55).

1-Hydroxy-1-ethynyl-3,3,5-trimethyl-cyclohexane used as starting material for the following preparation was prepared in accordance with W. Ziegenstein, "Aethinylierung und Alkinylierung", p. 9, Verlag Chemie (1963). The conversion into 1-(3,3,5-trimethyl-cyclohex-1-en-1-yl)-pent-4-en-1-one was performed according to the procedure described in pathway I, paragraph (d). The analytical data were as follows:

$n_D$=1.4838; $d^{20}$=0.9107

IR: 3080, 1670, 1645, 990 and 910 cm$^{-1}$;

NMR: 1.02 (3H, d, J=6 Hz), 1.08 and 1.1 (6H, 2s), 4.78–6.1 (3H, m), 6.4 (1H, m) δ ppm;

MS: M+ =206 (20); m/e: 191 (7), 177 (6), 151 (90), 123 (100), 81 (55), 55 (44), 41 (30).

1-(3,3-Dimethyl-cyclohex-6-en-1-yl)-hex-4-en-1-one (i), 1-(3,3-dimethyl-cyclohex-1-en-1-yl)-hex-4-en-1-one (ii), 1-(3,3-dimethyl-cyclohex-6-en-1-yl)-3-methyl-pent-4-en-1-one (iii) and 1-(3,3-dimethyl-cyclohex-1-en-yl)-3-methyl-pent-4-en-1-one (iv)

(Preparation according to pathway X)

The title compounds were prepared by analogy with the procedure indicated above for pathway I, starting from 7,11-dimethyl-7-hydroxy-dodeca-2,10-dien-5-yne. The analytical data were respectively as follows:

(i)

$n_D$=1.4921; $d^{20}$=0.9296

IR: 1670, 1640, 965 cm$^{-1}$;

NMR: 0.9 (6H, 2s), 1.6 (3H, d, J≃4Hz), 5.3 (2H, m) 6.68 (1H, m) δ ppm;

MS: M+ =206 (15); m/e: 191 (8), 177 (7), 137 (100), 109 (58), 81 (22), 67 (40), 41 (45).

(ii)

$n_D$=1.500; $d^{20}$=0.9378

IR: 1670, 1645, 965 cm$^{-1}$;

NMR: 1.02 (6H, 2s), 1.6 (3H, d, J≃5Hz), 5.3 (2H, m), 6.62 (1H, s) δ ppm;

MS: M+ =206 (15); m/e: 188 (12), 146 (90), 137 (100), 131 (55), 109 (75), 83 (48), 55 (60), 41 (65).

(iii)

$n_D$=1.4873; $d^{20}$=0.9202

IR: 3080, 1670, 1650, 1645, 990 and 910 cm$^{-1}$;

NMR: 1.01 (3H, d, J≃6Hz), 0.92 (6H, 2s), 4.7–6.1 (3H, m), 6.74 (1H, m) δ ppm.

(iv)

$n_D$=1.4889; $d^{20}$=0.9311

IR: 3080, 1665, 1635, 985 and 910 cm$^{-1}$;

NMR: 1.02 (3H, d, J≃7Hz), 1.11 (6H, 2s), 4.72–6.1 (3H, m), 6.4 (1H, m) δ ppm

MS: M+ =206 (8); m/e: 191 (3), 137 (100), 109 (65), 67 (30) 41 (32).

1-(3,3,5-Trimethyl-cyclohexa-1,5-dien-1-yl)-pent-4-en-1-one and 1-(3,3,5-trimethyl-cyclohexa-4,6-dien-1-yl)-pent-4-en-1-one (Preparation according to pathway XI)

The title compounds were prepared by analogy with the procedure described for pathway V, starting from 2,4,4-trimethyl-cyclohex-2-en-1-one.

1-(3,3,5-Trimethyl-cyclohexa-1,5-dien-1-yl)-pent-4-en-1-one $n_D$=1.5132; $d_4$=0.9612

IR: 3080, 1650, 1640, 1570, 990, 910 cm$^{-1}$;

MS: M+ =204 (8); m/e: 109 (14).

1-(3,3,5-Trimethyl-cyclohexa-4,6-dien-1-yl)-pent-4-en-1-one

IR: 3080, 1660, 1645, 1575, 990 and 910 cm$^{-1}$;

NMR: 0.94 (6H, 2s), 1.8 (3H, d, J≃2Hz), 2.22 (2H, d, J≃2Hz), 4.7–6.1 (3H, m), 5.53 and 6.61 (2H, 2s) δ ppm MS: M+ =204 (15); m/e: 189 (25).

1-(3,5-Dimethyl-cyclohex-6-en-1-yl)-pent-4-en-1-one (i), 1-(cis 3,4-dimethyl-cyclohex-6-en-1-yl)-pent-4-en-1-one (ii), 1-(trans 3,4-dimethyl-cyclohex-6-en-1-yl)-pent-4-en-1-one (iii)

and 1-(trans 3,4-dimethyl-cyclohex-1-en-1-yl)-pent-4-en-1-one (iv)

(Preparation according to pathway XII)

The title compounds were prepared by analogy with the procedure described for pathway VIII. The analytical data of the compounds thus obtained were as follows:

(i)

$n_D$=1.4881; $d^{20}$=0.9249

IR: 3075, 1665, 1640, 990 and 910 cm$^{-1}$;

NMR: 1.04 and 1.12 (6H, 2d, J≃7Hz), 2.2–2.9 (4H, m) 4.75–6.2 (3H, m) 6.55 (1H, m) δ ppm;

MS: M+ =192 (1); m/e: 191 (25), 177 (2), 137 (100), 109 (98), 67 (55), 55 (50), 41 (35).

(ii)

$n_D$=1.4929; $d^{20}$=0.9410

IR: 3080, 1665, 1640, 990 and 910 cm$^{-1}$;

NMR (90MHz): 0.85 and 0.87 (6H, 2d, J≃7Hz), 2.75 (4H, m), 4.9–6.1 (3H, m), 6.8 (1H, m) δ ppm;

MS: M+ =192 (6); m/e: 177 (4), 163 (2), 137 (100), 109 (40), 81 (15), 67 (43), 55 (38), 41 (36).

(iii)

$n_D$=1.4899; $d^{20}$=0.9292

IR: 3080, 1665, 1645, 995 and 910 cm$^{-1}$;

NMR: 0.98 (6H, 2d, J≃7Hz), 2.75 (4H, m), 4.88–6.1 (3H, m), 6.85 (1H, m) δ ppm;

MS: M+ =192 (7); m/e: 177 (4), 137 (100), 109 (40), 81 (18), 67 (38), 55 (30), 41 (25).

(iv)

$n_D$=1.4888; $d^{20}$=0.9290

IR: 3080, 1665, 1645, 992 and 910 cm$^{-1}$;

NMR: 1.04 (3H, d, J≈6Hz), 1.12 (3H, d, J≈8Hz), 2.75 (4H, m) 4.9–6.1 (3H, m) 6.65 (1H, m) δ ppm;

MS: M+ =192 (15); m/e: 177 (6), 151 (14), 137 (100), 121 (6), 109 (55), 85 (11), 81 (16), 67 (48), 55 (44), 41 (38).

1-(2,3,3-Trimethyl-cyclohexa-4,6-dien-1-yl)-pent-4-en-1-one (Preparation according to pathway XIII)

Pyronenols were obtained by thermolysis of myrthenol (cf. U.S. Pat. No. 2,821,547).

(a) 1-Hydroxymethyl-2,3,3-trimethyl-cyclohexa-4,6-diene was easily converted into the corresponding 1-formyl derivative by reduction with $LiAlH_4$.

(b) 7.5 g of the obtained aldehyde in 50 ml of ether were added under nitrogen and with external cooling to a Grignard solution prepared by 1.4 g of magnesium turnings and 8.1 g of 4-bromo-but-1-ene in 30 ml of ether. After having been refluxed for 1 hr, the reaction mixture was treated with iced water and the ethereal phase separated. The usual treatments of washing and evaporation gave 8.5 g of a diasteroisomeric mixture of 1-(2,3,3-trimethyl-cyclohexa-4,6-dien-1-yl)-1-hydroxy-pent-4-ene: b.p. 110°/0.1 Torr; $n_D$=1.5005; $d^{20}$=0.9328.

(c) 5.2 g of the obtained carbinol in 150 ml of petrolether (b.p. 30°–50°) were treated at room temperature under nitrogen with 60 g of $MnO_2$ and the reaction mixture was kept under stirring for 24 h. A bulb distillation (0.1 Torr) gave 4.8 g of the desired cyclohexadienic ketone which upon purification showed the following analytical characters:

$n_D$=1.5113; $d^{20}$=0.9627

IR=1665, 1640, 990, 910, 735 cm$^{-1}$;

NMR: 0.76 (3H, d, J≈7 cps); 0.9 and 1.06 (2s, 6H); 4.75–6.1 (3H, m); 5.75 (2H, m); 6.7 (1H, m) δ ppm;

MS: M+ =204 (9); m/e: 189 (18), 149 (38), 133 (35), 121 (50), 105 (40), 91 (41), 83 (40), 55 (100), 41 (60).

1-(2,3,3-Trimethyl-cyclohex-6-en-1-yl)-pent-4-en-1-one (Preparation according to pathway XIII)

(a) 30.4 g of 1-hydroxymethyl-2,3,3-trimethyl-cyclohexa-1,5-diene were hydrogenated at 10°–12° in the presence of 1g of Raney-nickel in 300 ml of ethanol. 3.95 l of hydrogen were thus absorbed within 2.5 h. A filtration followed by evaporation and distillation gave 28.2 g of 1-hydroxymethyl-2,3,3-trimethyl-cyclohex-5-ene. $n_D$=1.4862, $d^{20}$=0.9447

(b) 15.4 g of the obtained carbinol were oxidized at room temperature under nitrogen with 180 g of $MnO_2$ in 150 ml of petrol-ether (b.p. 30°–50°). After 24 h the reaction mixture was filtered, evaporated and bulb distilled at 12 Torr to give 12 g of 1-formyl-2,3,3-trimethyl-cyclohex-6-ene $n_D$=1.4879; $d^{20}$=0.9536

(c) By carrying out the reaction according to same procedure as that described in section (b) above for the preparation of 1-(2,3-dimethyl-cyclohexa-4,6-dien-1-yl)-pent-4-en-1-one, and starting from the above obtained formyl derivative (10 g), there were obtained 12.3 g of raw 1-(2,3,3-trimethyl-cyclohex-6-en-1-yl)-1-hydroxy-pent-4-ene as a (1:1) diastereoisomeric mixture:

$n_D$=1.4909; $d^{20}$=0.9298

(d) An oxidation by means of $MnO_2$ (60 g) on 5.2 g of the above obtained carbinol gave upon bulb distillation 4.8 g of 1-(2,3,3-trimethyl-cyclohex-6-en-1-yl)-pent-4-en-1-one having a purity of ca. 85%: b.p. 110°/0.01 Torr. A purification by means of vapour phase chromatography gave a sample showing the following analytical character:

IR: 3080, 1675, 1640, 990 and 910 cm$^{-1}$

NMR: 0.82 (3H, d, J≈7 cps); 0.8 and 0.93 (6H, 2s); 4.73–6.1 (3H, m); 6.65 (1H, t, J≈4 cps) δ ppm;

MS: M+ =206 (13); m/e: 191 (10), 163 (15), 151 (100) 123 (56), 107 (16), 95 (30), 81 (54), 67 (30), 55 (44), 41 (35);

$n_D$=1.4909; $d^{20}$=0.9296

The invention is better illustrated by the following examples.

EXAMPLE 1

A base perfume composition of the "chypre"-type was prepared by admixing the following ingredients (parts by weight):

| | |
|---|---|
| Synthetic Jasmin | 150 |
| Vetiveryl acetate | 60 |
| Synthetic rose of may | 10 |
| Synthetic bulgarian rose | 50 |
| Synthetic bergamot | 150 |
| Synthetic lemon | 50 |
| Angelica roots oil 10%* | 20 |
| α-Isomethyl-ionone | 80 |
| Cyclopentadecanolide 10%* | 50 |
| Muscone 10%* | 50 |
| γ-Undecalactone 10%* | 50 |
| Undecylenic aldehyde 10%* | 50 |
| Absolute oak moss 50%* | 50 |
| Dodecanal 10%* | 10 |
| Synthetic civet | 50 |
| Ylang extra | 20 |
| Sandal wood oil Mysore | 20 |
| Musk ketone | 20 |
| 1,1-Dimethyl-4-acetyl-6-ter-butylindane | 10 |
| Synthetic lily-of-the-valley | 50 |
| | 1000 |

*in diethyl phthalate

By adding to 95 g of the above indicated base, 5 g of a 10% * solution of 1-(3,3-dimethyl-cyclohex-6-en-1-yl)-pent-4-en-1-one, a novel composition was obtained. This composition possessed an original, harmonious tonality which proved to be distinctly more sophisticated than that shown by the base composition, it possessed moreover a green, herbal and lifting note which matches particularly well to the base odoriferous character.

By substituting 1-(3,3-dimethyl-cyclohex-1-en-1-yl)-pent-4-en-1-one for 1-(3,3-dimethyl-cyclohex-6-en-1-yl)-pent-4-en-1-one in the above Example, analogous results were observed. The effects achieved were however less marked.

EXAMPLE 2

A base perfume composition for after-shave lotion was prepared by admixing the following ingredients (parts by weight):

| | |
|---|---|
| Synthetic bergamot | 120 |
| p-ter-Butyl-cyclohexanone | 100 |
| Cedryl acetate | 100 |
| Methyl-octylacetaldehyde 10%* | 80 |
| Synthetic Jasmin | 60 |
| Lemon oil | 60 |
| Florida orange oil | 50 |
| "Mousse d'arbre" concrete 50%* | 50 |
| Absolute lavandin oil | 40 |
| Clove oil Madagascar | 40 |
| Trimethylcyclododecatriene epoxide | 40 |
| Synthetic Neroli | 40 |
| Undecanal 10%* | 20 |

-continued

| | |
|---|---|
| Styrallyl acetate | 20 |
| Patchouli oil | 20 |
| Isocamphyl cyclohexanol | 20 |
| α-Isomethyl-ionone | 20 |
| Dimethyl-cyclohexene-carbaldehyde | 20 |
| Total | 900 |

*in diethyl phthalate

By adding to 90 g of the above base composition, 10 g of a 1% * of 1-(3,3-dimethyl-cyclohex-6-en-1-yl)-pent-4-en-1-one, a novel composition was obtained. This composition possessed when compared to the base composition a fresher and more harmonious tonality with a more marked green and herbal top note.

By substituting in the above Example 1-(3,3-dimethyl-cyclohex-1-en-1-yl)-pent-4-en-1-one for the above indicated ketone, analogous although less marked effects were observed.

EXAMPLE 3

A base perfume composition for "eau-de-toilette" was prepared by admixing the following ingredients (parts by weight):

| | |
|---|---|
| Patchouli oil | 30 |
| Vetiveryl acetate | 50 |
| Synthetic Jasmin oil | 50 |
| Synthetic rose oil | 100 |
| Galbanum oil | 20 |
| Synthetic bergamot | 80 |
| Angelica roots oil 10%* | 20 |
| α-Isomethyl-ionone | 100 |
| Hydroxy-citronellal | 80 |
| Cyclopentadecanolide 10%* | 50 |
| γ-Undecalactone 10%* | 20 |
| Undecylenic aldehyde 10%* | 70 |
| Methyl-nonylaldehyde 10%* | 10 |
| Dodecanal 1%* | 20 |
| Phenylacetaldehyde 10%* | 20 |
| β-Damascone 10%* | 20 |
| Phenyl-methyl carbinol | 20 |
| Synthetic civet | 5 |
| Ylang | 25 |
| Sandal wood oil Mysore | 20 |
| Coumarin | 20 |
| Musk ketone | 30 |
| Oak moss 50%* | 20 |
| Eugenol | 40 |
| Lemon oil | 20 |
| Diethyl phthalate | 60 |
| | 1000 |

*in diethyl phthalate

By adding to 90 g of the above base 10 g of 1-(3,3-dimethyl-cyclohexa-1,5-dien-1-yl)-pent-4-en-1-one, a novel composition was obtained. This composition possessed, when compared to the base, an improved green and particularly pleasant note. Even at a concentration of 1%, the said composition achieved an analogous positive effect.

By replacing, in the above Example 1-(3,3-dimethyl-cyclohexa-1,5-dien-1-yl)-pent-4-en-1-one by one of the following compounds:
1-(3,3-dimethyl-cyclohex-6-en-1-yl)-pent-4-en-1-yl formate,
1-(3,3-dimethyl-cyclohex-6-en-1-yl)-hex-5-en-1-one,
prop-2-en-1-yl(3,3-dimethyl-cyclohex-6-en-1-yl)-carboxylate,
1-(3,3-dimethyl-cyclohexa-1,4-dien-1-yl)-pent-4-en-1-one
or 1-(4,4-dimethyl-cyclohex-1-en-1-yl)-pent-4-en-1-one, at concentrations ranging from 0.01% to 2% relative to the weight of the composition, new compositions possessing a more pronounced green and fruity character were obtained.

EXAMPLE 4

A base perfume composition for toilet soaps was prepared by admixing the following ingredients (parts by weight):

| | |
|---|---|
| Undecylenic aldehyde 10%* | 50 |
| Methyl-nonyl aldehyde 10%* | 20 |
| Methyl 1-(1-oxo-2-pentyl-cyclopentyl)-acetate 10%* | 20 |
| Synthetic ambra 10%* | 20 |
| Ethyl Methylphenylglycidate 10%* | 20 |
| Trichloro-methylphenyl carbinyl acetate | 20 |
| Coumarin | 30 |
| Heliotropine | 20 |
| 1,1-Dimethyl-4-acetyl-6-ter-butyl indane | 30 |
| Acetylcedrene | 60 |
| Phenylethyl-carbinyl acetate | 10 |
| Benzyl salicylate | 30 |
| α-Isomethyl-ionone | 60 |
| Patchouli oil | 10 |
| Hexylcinnamaldehyde | 50 |
| Phenyl-ethyl alcohol | 100 |
| Synthetic geranium | 50 |
| "Mousse d'arbre" concrete 50%* | 40 |
| Galbanum | 5 |
| Synthetic Ylang | 65 |
| Cyclamen aldehyde | 40 |
| Benzyl acetate | 50 |
| Synthetic bergamot | 200 |
| | 1000 |

*in diethyl phthalate

By adding to the above base one of the compounds indicated in Example 3 at the same concentrations as those given in the said Example or at concentrations up to twice these values, novel compositions with an improved diffusion power were obtained.

EXAMPLE 5

A base perfume composition for a "textile refreshing" perfume was prepared by admixing the following composition (parts by weight):

| | |
|---|---|
| Trimethyl-hexyl acetate | 140 |
| Benzyl acetate | 80 |
| α-Amyl-cinnamic aldehyde | 100 |
| Decanal 10%* | 10 |
| Undecanal 10%* | 10 |
| Undecanal 10%* | 20 |
| Dodecanal 10%* | 20 |
| Trimethyldecadienal 10%* | 20 |
| Benzyl salicylate | 80 |
| 1-Hydroxymethyl-4-isopropyl-cyclohexane | 70 |
| α-iso-Methylionone | 60 |
| Synth. rose | 60 |
| Lilial ®, Givaudan & Cie SA | 50 |
| 1,1-Dimethyl-4-acetyl-6-ter-butyl-indane 10%* | 50 |
| Exaltolide ®, Firmenich SA 10%* | 30 |
| Hydroxycitronellal | 20 |
| Rhubofix,**Firmenich SA | 20 |
| Undecalactone | 20 |
| Petitgrain oil | 10 |
| Galbanum residue | 20 |
| Linalool | 30 |
| | 920 |

*in diethylphthalate
**A mixture of 9-(12,13-epoxy-ethyl)-4-methyl- and 9(12,13-epoxy-ethyl)-5-methyl-tricyclo(6.2.1.0$^{2,7}$)-4,5-epoxy-undecane.

By adding to 92 g of the above composition 8 g of a 10% solution of 1-(2,3,3-trimethyl-cyclohex-6-en-1-yl)-pent-4-en-1-one in diethylphthalate, there was obtained a novel composition possessing a more flowery note. Its olfactive character was more pleasant with an enhanced top note of galbanum.

What is claimed is:

1. A compound of formula

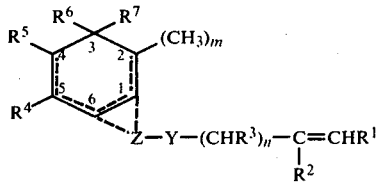

(I)

having a saturated ring or an isolated double bond in position 1, 4 or 6 or two double bonds in position 1 and 4, 1 and 5, or 4 and 6 of the ring as indicated by the dotted lines, and wherein:

m stands for integers 0 or 1;

n stands for integers 0, 1 or 2;

Z is bound to the ring carbon atoms in position 1 or 6 and represents the group —$COR^8$ or

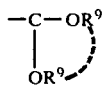

(wherein symbol $R^8$ represents an acyl group, and $R^9$s represent, when taken individually, an alkyl group having from 1 to 6 carbon atoms, or, when taken together, an alkylenyl group having from 2 to 6 carbon atoms);

Y represents a methylene group;

each of the symbols $R^1$, $R^2$, $R^3$, $R^4$ and $R^5$ designates a hydrogen atom or one of them represents a methyl radical and each of the others a hydrogen atom, and each of the symbols $R^6$ and $R^7$ represents an alkyl radical having from 1 to 3 carbon atoms or one of them represents an alkyl radical as defined above and the other a hydrogen atom.

2. 1-(3,3-Dimethyl-cyclohex-1-en-1-yl)-pent-4-en-1-yl acetate.

3. 1-(3,3-Dimethyl-cyclohex-1-en-1-yl)-pent-4-en-1-yl formate.

4. 1-(3,3-Dimethyl-cyclohex-1-en-1-yl)-1,1-ethylenedioxy-pent-4-ene.

5. 1-(3,3-Dimethyl-cyclohex-6-en-1-yl)-pent-4-en-1-yl acetate.

6. 1-(3,3-Dimethyl-cyclohex-6-en-1-yl)-pent-4-en-1-yl formate.

7. 1-(3,3-Dimethyl-cyclohex-6-en-1-yl)-1,1-ethylenedioxy-pent-4-ene.

8. A perfumed article comprising, as an odour-modifying ingredient, at least one compound according to claim 1.

9. A process for enhancing or improving the odoriferous properties of perfume compositions or perfumed products which comprises adding thereto at least one compound according to claim 1.

10. A perfume composition comprising at least one compound according to claim 1 together with a carrier or a diluent.

* * * * *